United States Patent [19]
Laurie et al.

[11] Patent Number: 5,696,229
[45] Date of Patent: Dec. 9, 1997

[54] POLYPEPTIDE WITH LAMININ CELL ADHESION AND MORPHOGENESIS ACTIVITY

[75] Inventors: Gordon W. Laurie, Charlottesville, Va.; Michelle L. Matter, La Jolla, Calif.; Lanlin Chen, Charlottesville, Va.

[73] Assignee: The University of Virginia Patent Foundation, Charlottesville, Va.

[21] Appl. No.: 405,200

[22] Filed: Mar. 16, 1995

[51] Int. Cl.[6] ................................................. A61K 38/03
[52] U.S. Cl. .................... 530/326; 530/327; 530/328; 530/329; 530/330; 514/13; 514/14; 514/15; 514/16; 514/17
[58] Field of Search ................ 514/13–17; 530/326–330

[56] References Cited

FOREIGN PATENT DOCUMENTS

| 0364690 | 4/1990 | European Pat. Off. |
| 9013562 | 11/1990 | WIPO |

OTHER PUBLICATIONS

Chassot, Virology 200, 72, 1994.

*Primary Examiner*—Cecilia J. Tsang
*Assistant Examiner*—David Lukton
*Attorney, Agent, or Firm*—Oblon, Spivak, McClelland, Maier & Neustadt, P.C.

[57] ABSTRACT

The present invention provides novel cell adhesion peptides.

18 Claims, 13 Drawing Sheets

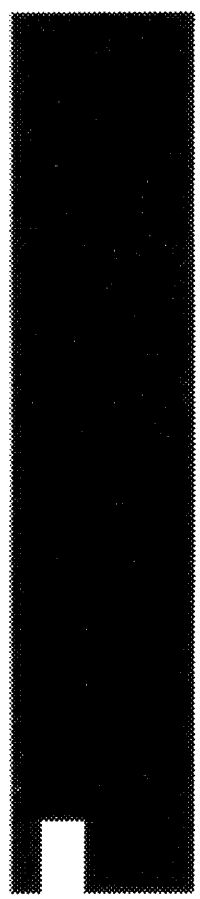
FIG.8A   FIG.8B   FIG.8C

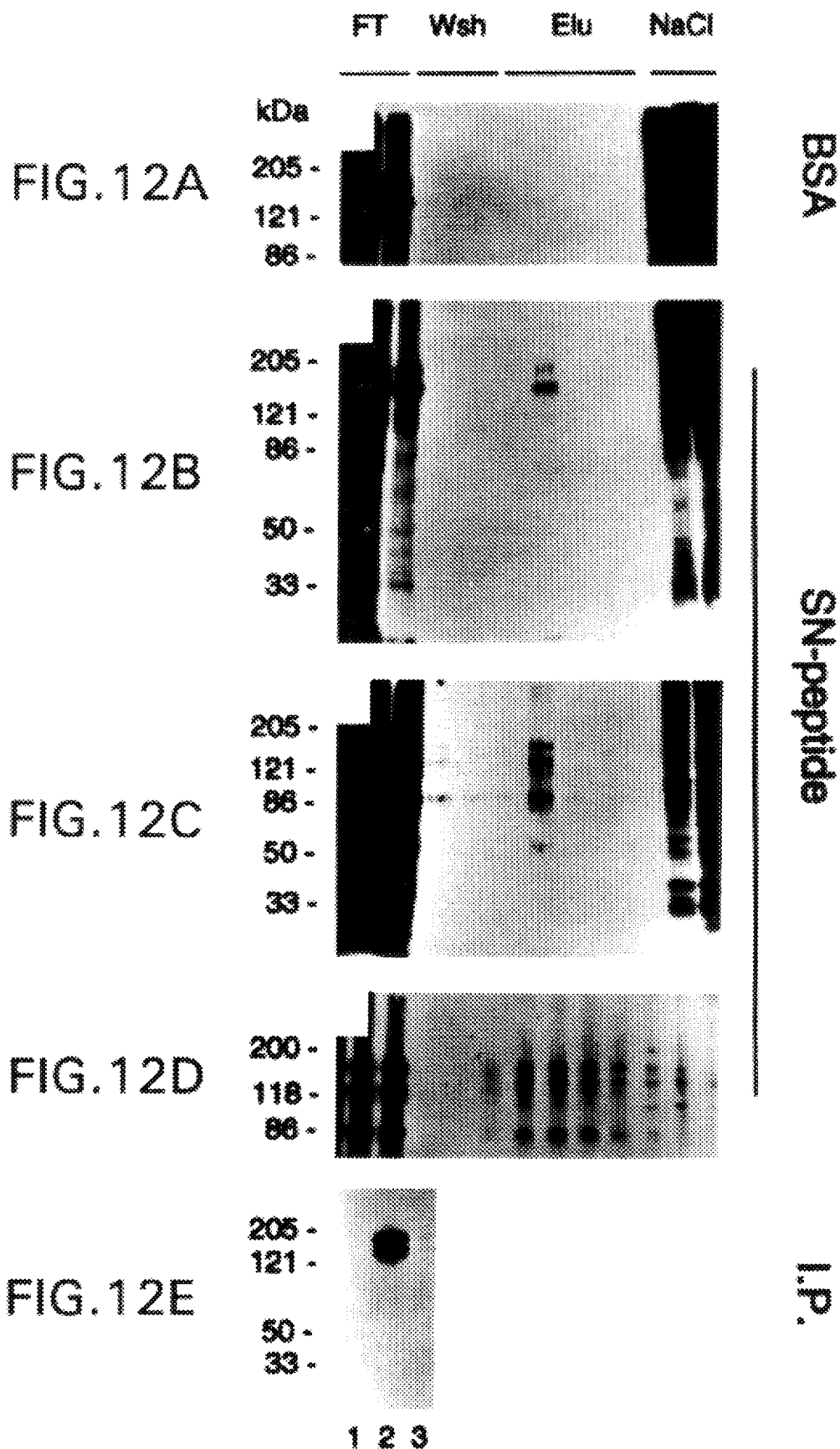

POLYPEPTIDE WITH LAMININ CELL ADHESION AND MORPHOGENESIS ACTIVITY

This research was in-part funded by a NIH grant. The government may have rights to this application.

BACKGROUND OF THE INVENTION

1. Field of the Invention

The present invention provides novel cell adhesion peptides. The peptides can be formulated into pharmaceutical compositions to speed wound healing and/or inhibit metastasis.

2. Discussion of the Background

Morphogenesis of lung alveoli, the functional unit of bi-directional gas directional gas exchange, occurs mainly postnatally with an increase of 280 million alveoli during the first eight years of human life (Thurlbeck, 1975). Alveoli arise initially from outgrowths of terminal air ducts, a process coincident with the appearance of basement membrane-adherent type II alveolar cells (Burri, 1991). Type II cells subsequently proliferate, coassemble and serve both as progenitors for attenuated type I alveolar cells (Mason and Williams, 1991) and later as the only source of pulmonary surfactant (Hawgood, 1991). A mature alveolus consists of a central air space lined by type II and type I alveolar cells which are adherent basally to a thin basement membrane (McGowan, 1992; Sannes, 1991; Lwebuga-Mukasa, 1991).

Previously, peptides with cell adhesion activity have been identified. U.S. Pat. Nos. 4,517,686; 4,589,079; 4,661,111 and 4,792,525 teach the peptide, RGDS (SEQ ID NO:1).

Iwamoto et al, Science (1987) 238:1132 and Graf et al, Biochem. (1987) 26:6896 teach the peptide, YIGSR (SEQ ID NO:14).

Sephel et al, Biochem. Biophys. Res. Commun. (1989) 162:821 and Tashiro et al, J. Biol. Chem. (1989) 264:16174 teach the peptide, IKVAV (SEQ ID NO: 22).

Liesi et al, FEBS Lett. (1989) 244:141 teach the peptide, RNIAEIIKDI (SEQ ID NO:23).

SUMMARY OF THE INVENTION

It is an object of the present invention to provide peptides which have useful biological activity in the field of cell adhesion and migration and blocking of tumor metastases.

It is a further object of the present invention to provide pharmaceutical compositions comprising the above peptides.

It is a further object of the present invention to provide a method of culturing cells in the presence of the above peptides.

It is a further object of the present invention to provide peptides which inhibit in vivo the migration of tumor cells in tissues.

It is a further object of the present invention to provide peptides which promote wound healing.

It is a further object of the present invention to provide peptides which promote alveolarization.

It is a further object of the present invention to provide alveolarized cell cultures.

It is yet another object of the present invention to provide peptides which block angiogenesis.

These and other objects have now been achieved by the inventors who have discovered that polypeptides of the sequence SINNNRWHSIYITRFGNMGS (SEQ ID NO:7) or PIDDNRWHSIHVARFGNIGS, and peptide fragments thereof, have biological activity in the field of cell adhesion and migration and blocking of tumor metastases (SEQ ID NO:10).

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 8A–8C. Presence of laminin A chain in fetal rat alveolar basement membranes. (A) Laminin A chain detected in fetal lung homogenate blot using ab-A[IK]. (B) Light micrograph of fetal rat lung incubated with Cy3-labeled secondary antibody alone, as compared with (C) incubation with ab-A[IK] followed by Cy3-labeled secondary antibody. Arrows indicate immunoreactive alveolar basement membranes. Bar, 50 µm.

FIGS. 12a–12c. α6β1 binds SN-peptide columns. Control BSA column (left panel) vs SN-peptide column (middle panel) after incubation with surface biotinylated F9 cell extracts. Columns were washed extensively, then eluted with EDTA. Left panel, first two EDTA fractions from BSA column. No material is eluted. Middle panel, all five EDTA fractions from BSA column. Two prominent bands are apparent in the eluate. Right panel:, GoH3 immunoprecipitation of pooled EDTA eluate from the SN-peptide column. The prominent upper band is α6 and the lower band β1. No material is immunoprecipitated with a rat IgG2a isotypic control antibody. Samples were separated by SDS PAGE (8%) under non-reducing conditions, transferred to nitrocellulose and detected with avidin peroxidase.

DETAILED DESCRIPTION OF THE PREFERRED EMBODIMENTS

Figure 1A:
FIGS. 1A–1C. Alveolar morphogenesis in vitro. (A) Negative control illustrating type II alveolar cells dispersed five days after plating on rat tail collagen I. (B) Alveoli formed five days after plating type II alveolar cells on BMS. Gelling concentration of all substrates here and throughout article 1.8 mg/cm$^2$. (C) Percentage of single cells declined as alveolar formation progressed (continuous lines). Proliferation was absent as revealed by daily analysis of cellular DNA content per well (dashed line). (Inset) Light micrograph of a representative sectioned day five alveolus illustrating central lumen. Values represent the means±SD; n=9. Bars; (A and B) 100 µm; (C) 10 µm.

The invention provides a polypeptide having the following sequence SINNNRWHSIYITRFGNMGS (SEQ ID NO:7) and peptide fragments thereof containing the subsequence SINNN (SEQ ID NO:8) or INNNR (SEQ ID NO:9), preferably containing the subsequence SINNNR (SEQ ID NO:4).

The invention also provides a polypeptide having the following sequence, PIDDNRWHSIHVARFGNIGS (SEQ ID NO:10), and peptide fragments thereof containing the subsequence PIDDN (SEQ ID NO:11) or IDDNR (SEQ ID NO:12), preferably containing the subsequence PIDDNR (SEQ ID NO:13).

The invention is also intended to include other polypeptides or substances containing this formula as well as polypeptides formed from the invention by limited substitution or deletion and which have cell attachment activity. Cell attachment activity hereinafter includes cell attachment promoting activity, phagocytic activity, and the inhibition of cell attachment. These peptides promote alveolarization, block angiogenesis, alter the formation of capillary structures by endothelial cells, prevent the formation of excess blood vessels in tissues, and inhibit in vivo tumor cell colonization of tissues.

The nomenclature used to define the polypeptide is conventional one letter abbreviations for L-amino acids as specified by Shroder & Lubke, "The Peptides", Academic Press (1965) wherein, in accordance with conventional representation the N-terminus appears to the left, and the C-terminus appears to the right.

Source of Peptides

The polypeptide, or a fragment thereof, can be synthesized by any suitable method, such as by exclusively solid-phase techniques, by partial solid-phase techniques, by fragment condensation or by classical solution-phase techniques. Moreover, synthesis may be carried out by recently developed recombinant DNA techniques.

Cell Attachment Promoting Activity

Although it is known that the entire polypeptide exhibits the desired cell-attachment activity, it is anticipated that fragments of the polypeptide will also be biologically active and will also exhibit the same, or substantially the same, cell-attaching activity, as is well known in the art of polypeptides; and accordingly, those biologically active fragments of the polypeptide are considered as constituting part of the invention.

The peptides of the present invention can be used as a cell-attachment protein to provide substrata to which cells will attach by treating a hydrophobic surface, such as untreated synthetic plastic resin material such as nitrocellulose, or comparable material, with the polypeptide. A similar substratum for cell attachment can be generated by coupling the polypeptide covalently to a solid support, such as glass or a synthetic plastic resin or a long chain polysaccharide, such as agarose, containing a reactive group that can bind the polypeptide. This latter approach can be effected by coupling the peptide to cyanogen bromide-activated agarose beads (sold under the trademark Sepharose by Pharmacia Fine Chemical, Uppsala, Sweden), sterilizing the beads by autoclaving, and thereafter showing that the peptide coating induces attachment of cells to the beads in a concentration greater than can be obtained by passive absorption.

It has also been found that the peptides of the present invention promote alveolarization in vivo. "Alveolarization" means that the treated cells assemble and form alveoli which are morphologically identical to those developed in fetal lung during late gestation. Suitable cells to be treated include stem cells or progenitor cells isolated from lung tissue, preferably either rat or human lung tissue, although lung tissue from any animal may be used. In this embodiment, the cells would be cultured in media containing the peptides of the present invention. Any conventional media which supports cell growth can be used (see for example those sold by Gibco). The preferred media is DMEM. The media may be supplemented with other soluble and insoluble factors to promote the alveolarization. Suitable soluble factors include, for example, fetal calf serum, prostaglandin, hydrocortisone, triiodothyronine, selenium, insulin, insulin growth factor I, Wnt-1, Wnt-4, fibroblastic growth factor, hepatocyte growth factor and combinations thereof. Suitable insoluble factors include, for example, Type I collagen, Type IV collagen, laminin, proteoglycans, fibronectin, pronectin-F, pronectin-L, recombinent adhesion molecule and combinations thereof.

The peptides of the present invention can also be used for preparing surfaces for optimal cell culture, derivatization of various prosthetic materials to promote bonding with surrounding tissues, providing for the increased internalization of molecules such as toxins, drugs, hormones, or the like by the enhancement of phagocytosis, and the development of ways of manipulating cellular adhesion mechanisms in diseases such as cancer metastasis and platelet aggregation.

Such substrata are useful in cell cultures where it is desirable to ensure proper attachment of the cells. Attachment proteins such as laminin have been shown to be important for the growth of many types of cells in vitro. Chemically defined media are often supplemented by attachment proteins (see for example, Barnes et al., Cell (1980) 22: 649–655). Coating of the culture substratum with the cell-attachment peptide would obviate the use of laminin in the medium, thus providing better defined conditions for the culture, as well as better reproducibility.

An example of the commercial use of cell attachment surfaces is the Cytodex particles manufactured by Pharmacia, wherein the particles are coated with gelatin, making it possible to grow the same number of adherent cells in a much smaller volume of media than would be possible in dishes. The activity of these beads is, however, dependent upon the use of laminin in the growth medium in most cases. The cell-attachment peptide of the present invention should provide a chemically defined coating for such purposes.

Alternatively, instead of cell-attachment to particles, the peptides of the present invention can be directly absorbed onto a conventional cell culture plate, preferably composed of a plastic. In this embodiment, the peptide would be suspended in water and contacted with the cell culture plate for a time sufficient to allow the peptide to absorb thereto, preferably overnight.

Medical devices can be designed which make use of such substrata to attract cells to the surface in vivo or even to promote the growing of a desired cell type on a particular surface prior to grafting. An example of this is endothelial cell growth on a prosthetic blood vessel or vascular graft, which is generally woven or knitted from polyester fiber, particularly Dacron fiber (a polyethylene terephthalate). Because most types of cells are attracted to laminin and to the peptides of the present invention, the peptides of the present invention are useful in coating a patch graft or the like for aiding wound closure and healing following an accident or surgery. The peptides of the present invention can also be used in coating surfaces of a prosthetic device which is intended to serve as a temporary or semipermanent entry into the body, e.g., into a blood vessel or into the peritoneal cavity, sometimes referred to as a percutaneous device. In such cases, it may be advantageous to couple the peptide to a biological molecule, such as collagen, a glycosaminoglycan, or a proteoglycan.

Application of the ability of the invention to inhibit cell attachment when presented in a solubilized form may find utility in situations where it is desirable to prevent cell adhesion to a substrate or adhesion between cells. Undesirable cell attachment to various medical sutures, or dressings, may be prevented by presenting the invention in solubilized form. When the invention is used either in conjunction or combination with another molecule, such as a therapeutic agent, or particle treated with such an agent, the entrance of that agent or particle into the cell may be enhanced by the effect of the invention on the phagocytic activity of the cell, thereby increasing the efficiency of the therapeutic agent. An example of one such application is the administration of the peptides of the present invention to inhibit angiogenesis.

Alternatively, the peptides of the present invention can be formulated into a pharmaceutical composition for administration to a patient.

The peptides of the present invention can be administered in any suitable amounts which will depend on the size, weight, extent of injury, etc. of the patient. In general, the amount will range from about 10 micrograms to about 20 milligrams per kilogram of body weight.

The peptides of the present invention may be used in the form of a liquid, such as eye drops or lotions, or a salve or gel which may be applied to promote cell attachment, an oral or intravenous formulation or in any any other convenient form. Accordingly, the peptides may be contained in any pharmaceutically acceptable carrier which is appropriate for the delivery means intended.

Obviously, numerous modifications and variations of the present invention are possible in light of the above teachings. It is therefore to be understood that within the scope of the appended claims, the invention may be practiced otherwise than as specifically described herein.

EXAMPLES

Example 1

Materials and Methods

Preparation of Substrates

Basement membrane substrate (BMS) was prepared at 4° C. in the presence of NEM (0.5 mM) and PMSF (0.5 mM)

by extraction of Engelbreth-Holm-Swarm (EHS) mouse tumor with 10 mM EDTA in 50 mM tris, 150 mM NaCl, pH 7.4 according to the method of Paulsson et al. (1987). Briefly, EHS tumor, collected from C57B1 or 1CR (Hilltop Lab Animals, Inc., Scottsdale, Pa.) mice, was homogenized, washed in 150 mM MACl, 50 mM Tris, pH 7.4 (TBS), and extracted overnight in TBS containing 10 mM EDTA (1 ml/gm tumor starting material). BMS, comprising the solubilized material, was then sterilized by dialysis against TBS containing chloroform (5 ml/l). Subsequent dialysis steps were against TBS and finally against three charges of DME. BMS protein concentration (8–10 mg/ml) was determined by lyophilization versus an equal volume of DME. BMS was stored as 1-ml aliquots at −80° C.

For gel filtration (4° C.) BMS was passed over a Biogel A 1.5-m column (2.5×100 cm; Bio Rad Laboratories, Melville, N.Y.) equilibrated in TBS containing 10 mM EDTA and proteolytic inhibitors. Fractions making up each of the two peaks (Paulsson et al., 1987) were pooled, concentrated (if necessary on an Amicon YM1 membrane [Amicon Corp., Beverly, Mass.]), sterilized with chloroform, and dialyzed against DME.

Mouse laminin and collagen IV were kindly supplied by Dr. R. Ogle (University of Virginia, Charlottesville, Va.). Mouse enractin was purchased from Upstate Biotechnology, Inc. (Lake Placid, N.Y.). Rat tail collagen I was purchased from Collaborative Research Inc. (Bedford, Mass.). Protein concentration of laminin and collagen IV was determined using their respective extinction coefficients (laminin: 8.3 ($A^{1\%}$ 1 $cm_{280}$), (McCarthy et al., 1983); collagen IV: 5.48 ($A^{1\%}$ $cm_{230}$)). Protein concentration of entactin and collagen I was used as supplied by the manufacturer.

Preparation of Antibodies

Rabbit anti-mouse laminin (ab-Ln) and rabbit anti-mouse collagen IV antisera were produced on contract with Hazelton Labs (Denver, Pa.). Rabbit anti-mouse entactin antibodies were obtained from Upstate Biotechnology, Inc. All antisera were purified on protein A-Sepharose (Pharmaceia Fine Chemicals, Piscataway, N.J.) before use; concentration of eluted antibody was calculated using the extinction coefficient for rabbit IgG (13.5 [$A^{1\%}$1 $cm_{280}$])/Ab-Ln and anti-collagen IV antibodies inhibit cell adhesion to laminin and collagen IV, respectively. Chain specific rabbit anti-mouse laminin polyclonal antibodies were kindly provided by Dr. Y. Yamada (NIDR, Bethesda, Md.), purified on protein A-Sepharose (Pharmacia Fine Chemicals), and checked for specificity by Western blotting. These antibodies are: (a) ab-B1 (antigen is a fusion protein spanning amino acids 925–933 which includes the UBGSR YIGSR (SEQ ID NO:14) sequence; previously designated HK-58); (b) ab-B2 (antigen is synthetic peptide consisting of amino acids 1420–1439; previously designated YY-13); (c) ab-A[IK] (antigen is a synthetic peptide consisting of amino acids 2097–2108; previously designated PA22-2 in Sephel et al. (1989)); (d) ab-A[SN] (antigen is synthetic peptide consisting of residues 2179–2198; previously designated PA10 in Sephel et al. (1989)). The rat anti-mouse monoclonal anti-laminin antibodies 5D3, 5A2 and 5C1 were kindly provided by Dr. D. Abrahamson (University of Alabama, Birminham, Ala.) (Abrahamson et al., 1989).

For Western blotting, DTT-reduced laminin was separated on 5% SDS-PAGE gels, transferred to nitrocellulose, blocked, incubated with anti-laminin antibody, washed and detected with peroxidase-labeled goat anti-rabbit IgG (Jackson ImmunoResearch laboratories, Inc., West Grove, Pa.) using the chemiluminescent ECL method (Amersham Corp., Arlington Heights, Ill.). Preabsorption of secondary antibody on a BMS-Sepharose column was necessary to eliminate background.

Laminin Fragments and Synthetic Peptides

Fragments E8 and P1, isolated from mouse laminin, were both kindly provided by Drs. Rupert Timpl (Max Planck Institute Fur Biochemie, Martinsried, Germany) and Peter Yurchenco (Robert Wood Johnson Medical School, Piscataway, N.H.). SN-peptide (SINNNRWHSIYTYRFGNMGS (SEQ ID NO:7); amino acids 2179–2198 from mouse laminin A chain) was synthesized by the Biomolecular Research Facility (University of Virginia), purified by reverse phase HPLC, and verified through NH$_2$-terminal sequencing. To attempt to determine the minimal active length, SN-peptide (SEQ ID NO:7) (10 mg) was incubated with TPCK treated trypsin (Washington Biochemical Corp., Freehold, N.J.) for 18 hours at 37° C. giving rise to three smaller peptides. Digestion was terminated by lowering the pH to 2.0; fragments were purified by reverse phase HPLC and sequenced. Examination of SN-peptide (SEQ ID NO:7) and SINNNR (SEQ ID NO:4) conservation among species made use of Fast A and BestFit searches (Dayhoff et al., 1978).

The HPLC purified peptide AASIKVAVSADR (SEQ ID NO:15) (amino acids 2097–2109 from mouse laminin A chain) and its scrambled control AA SVVIAKSADR (SEQ ID NO:16) were kindly supplied by Dr. Y. Yamada (Tashiro et al., 1989). Peptide KQNCLSSRASFRGCVRNLRLSR (amino acids 3011–3032 from mouse laminin A chain, previously designated GD-6 (Gehlsen et al., 1992), corresponding to the proposed $\alpha_3\beta_1$ integrin binding site, was kindly provided by Dr. K. Gehlsen (California Institute for Biological Research, La Jolla, Calif.). RGDS (SEQ ID NO:1) (functionally identical to RGDN (SEQ ID NO:20); amino acids 1123–1126 from mouse laminin A chain) was provided by Dr. R. Ogle (University of Virginia).

Isolation of Type II Alveolar Cells

Type II alveolar cells were isolated from 250-$_g$ Sprague Dawley rats (Hilltop Laboratory Animals, Inc.) according to the method of Rannels (Rannels and Rannels, 1988). Briefly, an initial cardiac perfusion with 0.9% saline was followed by instillation of the airways with 0.1% elastase (Calbiochem Corp., La Jolla, Calif.) in Joklik's modified minimal medium (JMEM) containing 0.05% BaSO$_4$. Elastase was inactivated by instillation of JMEM containing soybean trypsin inhibitor (0.08%; Sigma Chemical Co., St. Louis, Mo.), DNase (0.08%. Sigman Chemical Co.), and 50% newborn calf serum (GIBCO BRL, Gaithersburg, Md.). Lung tissue was minced, vortexed, and filtered through 160-μm nylon mesh (Tetko, Elmsford, N.Y.). Released cells were centrifuged for 10 min at 500 g, resuspended in JMEM containing 0.08% DNAse, and layered on a Percoll (Pharmacia Fine Chemicals) discontinuous density gradient. After centrifugation for 20 min (4° C.), cells were collected at the 1.04/1.08 interface, washed in JMEM, brought up in DME containing 10% fetal bovine serum (FBS) (GIBCO BRL), and incubated for 30 min (37° C.) in 75-cm$^2$ tissue culture flasks to eliminate contaminating macrophage cells which rapidly adhere to the plastic surface. The resultant type II alveolar cell preparations were 95% viable as determined by trypan blue exclusion; purity was 93% as assessed by the presence of lamellar bodies visible with Hoffman optics at a magnification of 40 and by tannic acid staining. Analysis of total cellular DNA/well on each day of an experiment was performed in triplicate on trypsin/disease released cells using a DNA fluorometry assay (Labarca and Paigen, 1980). No contaminating DNA could be detected in wells containing BMS alone, which after dissolution with dispase and trypsin did not contribute to the cell pellet.

Alveolar Formation Studies

Freshly isolated type II alveolar cells were plated in 96-well plates at $20\times10^3$ cells/well on 500 µg/well (1.8 mg/cm$^2$) of gelled BMS of collagen I. Cells were cultured over 5 d with on media change performed on day three. Alveolar formation was analyzed at 24-h intervals over 5 d from photographic negatives (4×original magnification of central portion of each well) of triplicate wells. Images from negatives were transferred via video camera to an Image I imaging system (Universal Imaging Corp., West Chester, Pa.) and viewed on a color video monitor. The area of cellular structures was then determined and expressed as the mean±standard deviation. In some cases two size categories were distinguished: (a) single cells (200–300 µm$^2$) and (b) model alveoli ($20\times10^3$ µm$^2$ or greater) with data expressed as percent of area occupied by each category.

To examine sectioned cultures, type II alveolar cells were plated on gelled GMS (500 µg/insert) supported by Millicell 0.4 µm filter inserts (Millipore Corp, Medford, Mass.). After 5d, cultures were fixed for 1 h with 2% formaldehyde/2% glutaraldehyde in 0.05M sodium phosphate buffer, pH 6.8, and washed. Filters were cut out, treated for 1 h with 1% osmium tetroxide, acetone dehydrated, and embedded in Spurr's resin (Electron Microscope Sciences, Ft. Washington, Pa.). Semi-thin or thin sections were then cut, stained and examined in the light or electron microscope, respectively.

In alveolar inhibition studies, antibodies (50 µg/well) were incubated with gelled BMS (500 µg/well) in wells of 96-well plates for 60 min at 37° C. Unbound antibody was removed by three DME washes (200 µl/well) and then freshly isolated cells were added. Dose-response assays were performed on all antibodies. Laminin fragments and synthetic peptides (micromolar amount indicated on figures) were preincubated with freshly isolated type II alveolar cells in suspension for 30 min at 37° C. with gentle agitation every 5 min; cells together with fragment or peptide were then plated on BMS. Cell viability in the presence of each antibody, fragment, or synthetic peptide was accessed using the MTT (3-[4,5-dimethylthiazol-2-yl]-2,5-diphenyl tetrazolium bromide) assay (Chemicon International, Inc. Temecula, Calif.).

Cell Adhesion Studies

Plates coated overnight (4° C.) with equimolar amounts of laminin, laminin fragment, or synthetic peptide were blocked with 1% BSA (Sigma Chemical Co.) for 4 h (4° C.) and cells were subsequently added ($2\times10^4$/well) in serum-free media and incubated for 60 min (37° C.) according to the method of Aumailey and Timpl (1986). Inhibition studies were carried out by preincubating cells for 30 min (37°; gentle agitation every 5 min) with equimolar amounts of soluble fragment or peptide. Cells, together with soluble inhibitor, were then added to the coated plates. After a 60-min (37° C.) incubation, plates were washed twice with PBX, fixed with 1% glutarldehyde (Electron Microscopy Service Laboratories, Westmount, N.J.), PBS, washed, stained with 0.1% crystal violet (Serra Biochemicals, Hauppauge, N.Y.), washed twice with distilled water, solubilized in 0.5% Triton X-100 (Sigma Chemical Co.), and read on an ELISA plate reader (Molecular Devices Corp., Menlo Park, Calif.) equipped with a 595-nm filter.

Immunohistochemistry

Immunostaining was performed on unfixed frozen sections of late gestation rat lung. Sections were blocked with 3% BSA (Sigma Chemical Co.) and then incubated with ab-A[IK] (rabbit anti-laminin A chain peptide [2097–2108]; 1 µg/ml) overnight at 4° C. Detection was through Cy3-labeled goat anti-rabbit IgG (I/50; Jackson Immunoresearch) that had been preadsorbed to gelled BMS for 30 min at 37° C. (Streuli et al., 1991). Slide preparations were washed and examined with a fluorescence microscope using a Rhodamine far red filter, ab-A[SN] (rabbit anti-laminin A chain peptide [2179–2198]), gave the same pattern but was much lighter.

Results

Role of Basement Membrane in Model Alveolar Formation

Figure 1B:
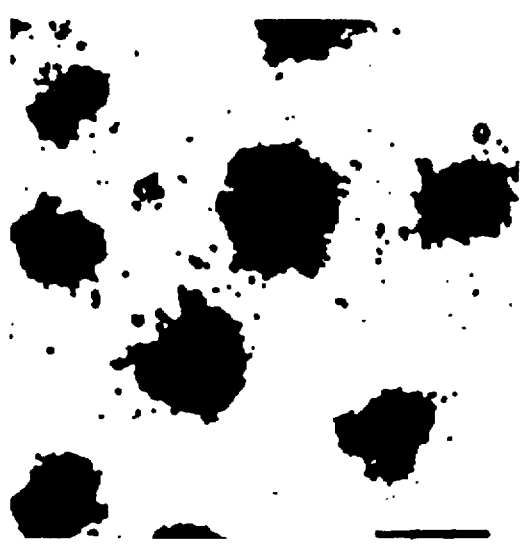
Figure 1C:
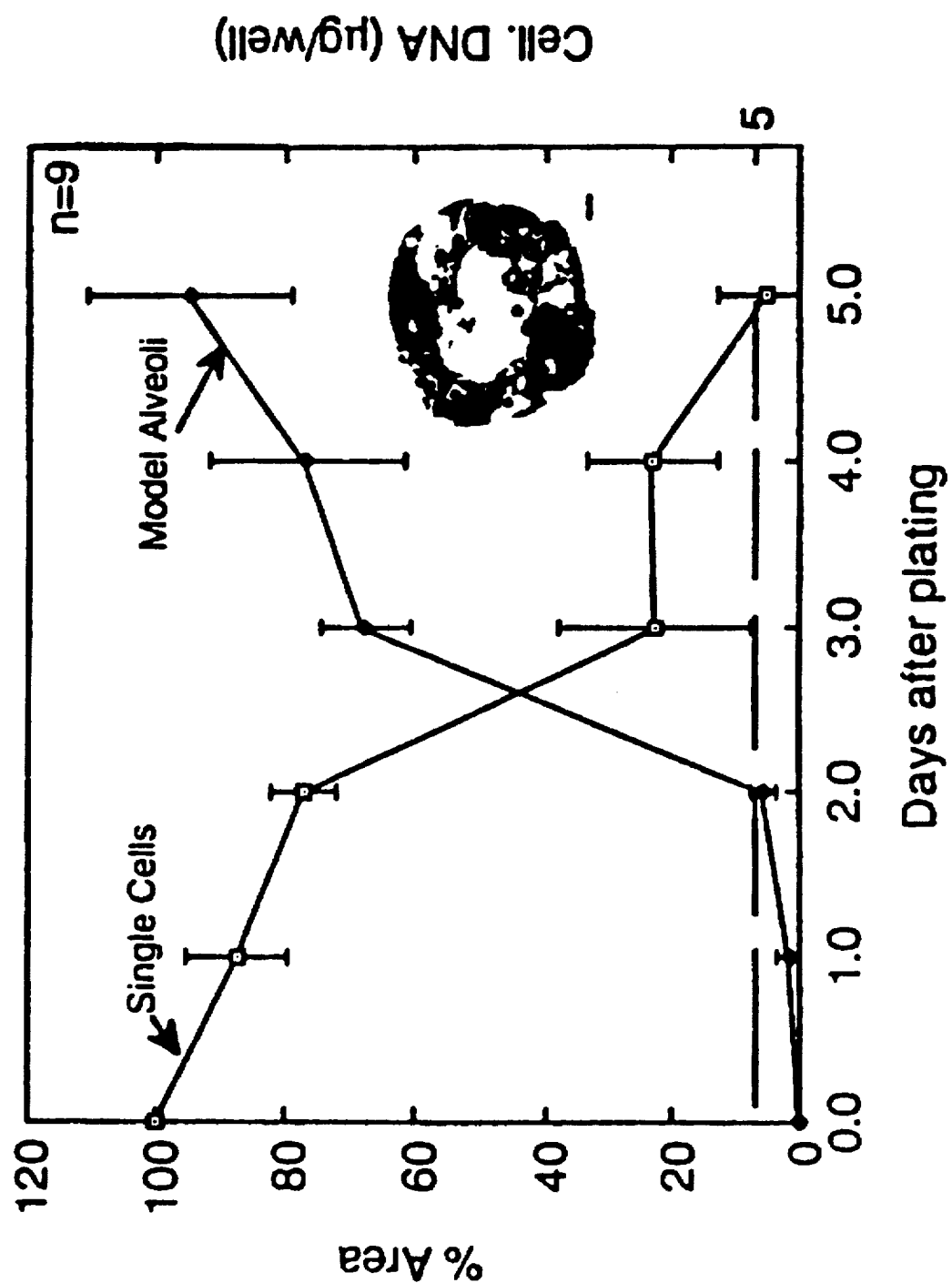
Figure 2A:
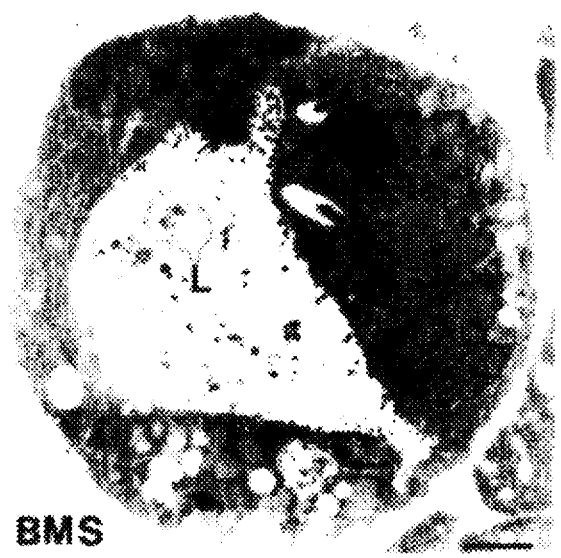
FIGS. 2A–2B. (A) Electron micrograph sectioned day five alveolus illustrating cuboidal type II alveolar cell lining similar to fetal alveoli. Alveolus is surrounded by BMS. Arrow points to characteristic lamellar body. L, central lumen. (B) Electron micrograph of type II alveolar cell within day five alveolus. Presence of circular lamellar bodies (arrows) and apical microvilli (arrowheads) are characteristic of type II alveolar cells in vivo. Bars: (A) 30 µm; (B) µm.
Figure 2B:

Alveoli-like structures become (FIGS. 1 and 2) apparent 3–5 d after plating dispersed type II alveolar cells on gelled BMS, a 10-mM EDTA extract of mouse EHS tumor basement membrane. These structures have a central lumen (FIG. 1C, inset; and FIG. 2AZ A) lined by a cuboidal epithelium of lamellar body containing (FIG. 2, A and B) type II alveolar cells. Type II cells are of appropriate polarity and therefore bear a striking resemblance to their in vivo fetal counterparts prior to the appearance of type I cells (Adamson and Boden, 1975). Morphogenesis was not dependent on cell proliferation (FIG. 1C) and was basement membrane specific since replacement with an equal milligram amount of gelled collagen I was completely ineffective (compare (FIG. 1, A and B).

Basement membranes are a partially characterized source of cell attachment, structural, and growth factor-like molecules (Paulsson, 1992). To determine which molecule or combination of molecules contributed to this process, BMS was separated into high and low molecular weight peaks by gel filtration and placed type II alveolar cells on each peak. Only the high molecular weight peak was active (not shown). Since constituents of the high molecular weight peak are laminin and entactin, interspersed with collagen IV (Paulsson et al., 1987), type II alveolar cells were plated on equal milligram amounts of each of these substrates and found that alveoli formed only on laminin (Table I), although smaller in size (since alveoli which formed on peak 1 or on laminin were smaller than alveoli on intact BMS, molecules of the low molecular weight peak may have an accessory role in modulating alveolar size) than an alveoli that formed on undivided BMS.

TABLE I

Effect of Laminin and Anti-Laminin Antibodies on Alveolar Formation in vivo

| Protein or antibody | Area (µm$^2$ × 10$^3$) |
| --- | --- |
| BMS | 108 ± 23 |
| Laminin | 35 ± 3 |
| Entactin | 1 ± 0.5 |
| Collagen IV | 0.4 ± 0.2 |
| Anti-Laminin (ab-Ln) | 12 ± 3.9 |
| Anti-Entactin | 105 ± 15 |
| Anti-Collagen IV | 110 ± 25 |

Type II alveolar cells were plated on 1.8 mg/cm$^2$ gelled BMS, laminin, entactin, or collagen IV; or on the same concentration of BMS which had been preincubated with 50 µg/well ab-Ln, anti-entactin, or anti-collagen IV antibodies. 5 d later, area or cellular structures was determined. Data is expressed as the mean of three experiments performed in triplicate ± SD. Alveoli are defined as structures > 20 × 10$^3$ µm$^2$.

These experiments were supported by parallel use of BMS preincubated with IgGs purified from either anti-laminin, anti-entactin, or anti-collagen IV sera. Only ab-Ln was inhibitory (Table I), a result consistent with an earlier observation that polyclonal anti-laminin anti-serum blocks Matrigel (Matrigel (Collaborative Research Inc. ) is a 2M urea extract of EHS tumor (Kleinman et al., 1986)) inhibition of type II alveolar cell spreading (Rannels et al., 1987).

Inhibition of Alveolar Formation by Fragment E8

Figure 3:
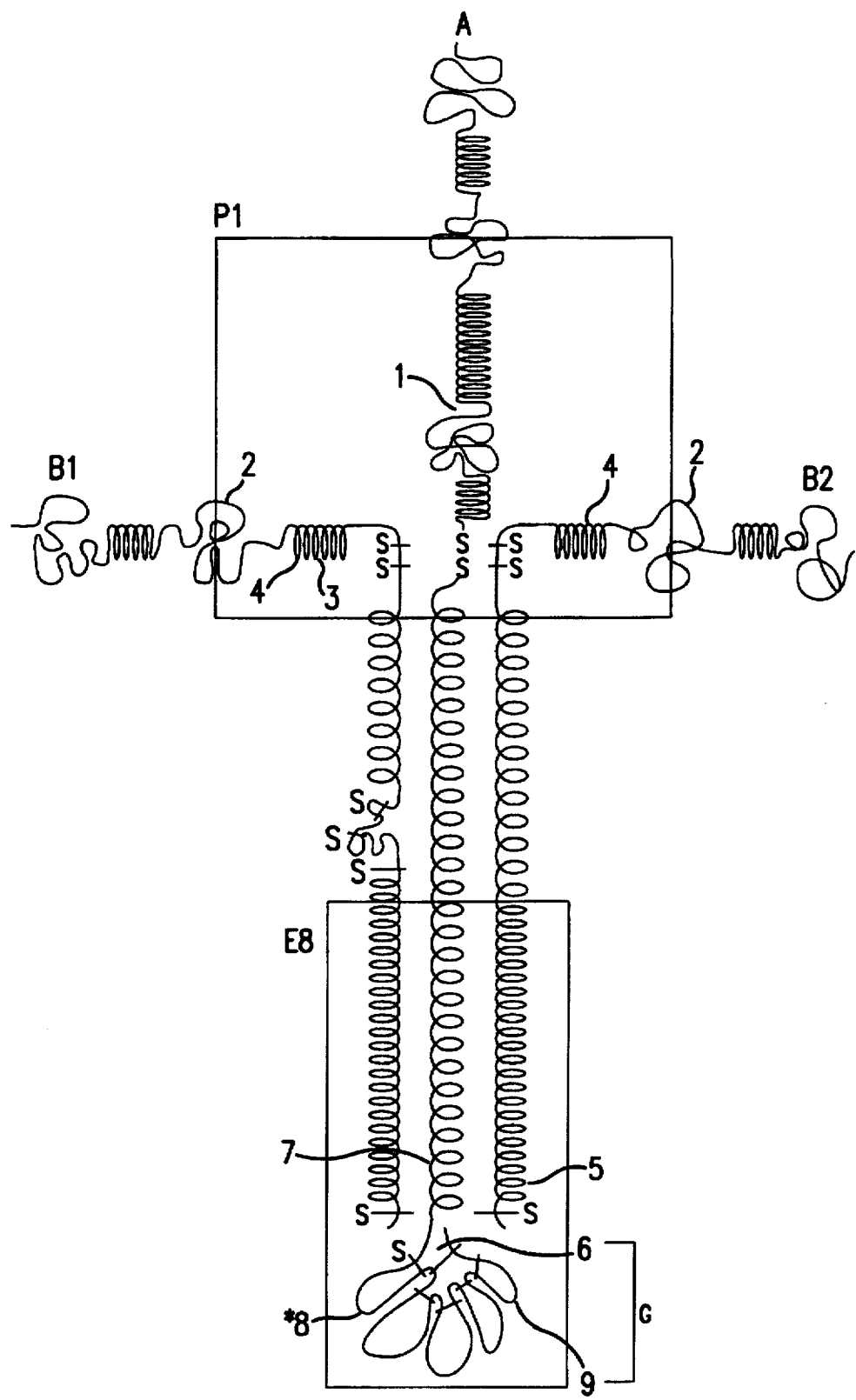
FIG. 3. Schematic diagram of laminin illustrating constituent B1, B2 and A chains; and origin of P1 and E8 fragments. G domain is the large A chain carboxy-terminal globule. Arrows indicate antibody, binding sites or origin of peptides tested: 1, RGDS (SEQ ID NO:1); 2, 5A2; 3, aB-B1; 4, 5C1; 5, ab-B2; 6, AASIKVAVSADR (SEQ ID NO:2) or ab-A[IK]; 7, 5D3; 8, ab-A[SN] or SN-peptide (SEQ ID NO:7); 9, KQNCLS-SRASFRGCVRNLRLSR. See Materials and Methods for details on antibodies and peptides, Laminin diagram modified from Sasaki et al. (1988), with permission (SEQ ID NO:3).

Laminin is a large cross-shaped cell adhesive eterotrimer (FIG. 3; Beck et al., 1990; Engel, 1992). Several large laminin domains have been partially characterized through the preparation of functional proteolytic fragments, particularly the P1 pepsin fragment and the E8 elastase fragment, whose respective origins on the intact molecule are known (FIG. 3).

Figure 4:
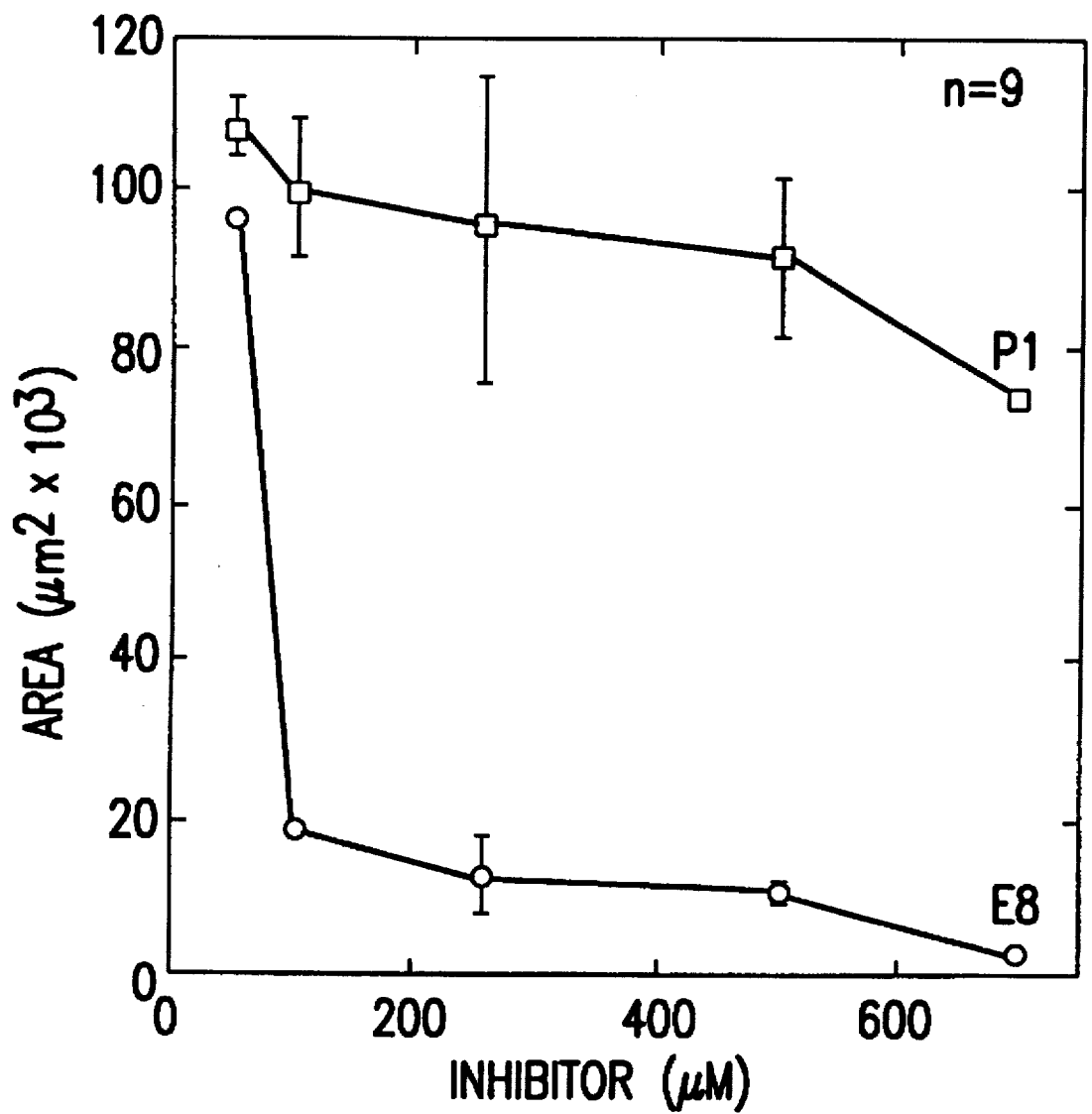
FIG. 4. Alveolar formation is inhibited by E8 but not P1 fragment. Dose-dependent inhibition of alveolar formation by soluble E8 but not P1 fragment. Freshly isolated type II alveolar cells were preincubated with E8 or P1 fragment prior to plating on BMS. Analysis was performed on day five. Values represent the mean±SD; n=9.

To determine whether in vitro alveolar promoting activity resides in laminin P1 or E8 region(s), type II alveolar cells were preincubated with increasing micromolar amounts (FIG. 4) of soluble P1 or E8 fragment prior to plating on BMS. Only fragment E8 was inhibitory (FIG. 4), an effect which was not due to lower cell viability (viability 85±3% at 700 µM) nor to decrease in the number of adherent cells (not shown); adhesion is presumably mediated through alternative sites in laminin or compensated by collagen IV or attachment factors present in the lower molecular weight peak.

Figures 5A, 5B:
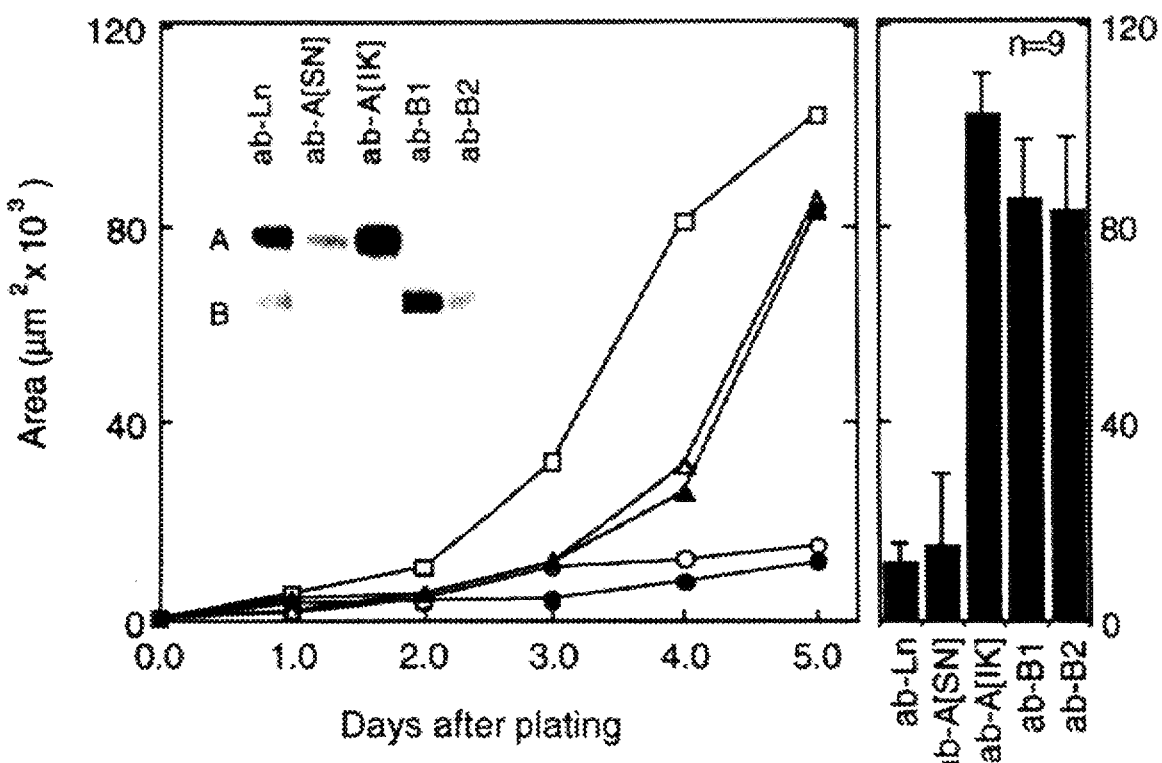
FIGS. 5A–5B. Alveolar formation is inhibited by an antibody directed against SN-peptide (SEQ ID NO:7) in the first loop of the E8 region G domain. (A) Time course inhibition of alveolar formation by ab-Ln (●) and ab-A[SN] (○). Ab-A[IK] (□), ab-B1 (△), and ab-B2 (▲) had little or no effect; t test for ab-B1 and ab-B2 on day four vs BMS alone revealed p values of 0.3, whereas p value for ab-A[SN] on day four was 0.015. Antibodies were protein A-Sepharose purified prior to incubation with BMS; type II alveolar cells were plated after washing away unbound antibody. (Inset) Western blot analysis of antibody specificity. (B) Inhibition of alveolar formation by ab-Ln and ab-A[SN], expressed as the mean±SD of analysis performed on day five; n=9.

Fragment E8 represents the 250-kD carboxy-terminal one third of laminin with its constituent B1, B2 and A chains. To locate the active site within E8, a number of chain specific (FIG. 5A, inset) antibodies prepared against synthetic peptides or fusion proteins, and several monoclonal antibodies whose binding sites (FIG. 3) had been mapped through rotary shadowing were obtained. BMS was preincubated with equal microgram amounts of purified antibody, unbound antibody was washed away, and cells were plated. As a positive control, equal microgram amounts of ab-Ln against intact laminin which, as mentioned above (Table I), was used and was inhibitory (FIG. 5). All antibodies prepared against sites within the P1 region were inactive, as were all but one of the anti-E8 fragment antibodies (FIG. 5; Table II).

TABLE II

Lack of Effect of Several Monoclonal Anti-Laminin Antibodies and Laminin A Chain Synthetic Peptides on Alveolar Formation in vitro

| Antibody or peptide | Area ($\mu m^2 \times 10^3$) |
| --- | --- |
| None | 108 ± 23 |
| 5D3 | 63 ± 18 |
| 5A2 | 83 ± 25 |
| 5C1 | 103 ± 20 |
| AASIKVAVSADR (SEQ ID NO: 15) | 98 ± 22 |
| AASVVIAKSADR (SEQ ID NO: 16) | 100 ± 18 |
| KQNCLSSRASFRGCVRNLRLSR (SEQ ID NO: 17) | 110 ± 19 |
| RGDS (SEQ ID NO: 1) | 105 ± 24 |

Complete inhibition occurred with ab-A[SN] raised against a 20-amino acid synthetic peptide (2179–2198) corresponding to a site (FIG. 3, *8) within the first loop of the large globule (designated "G domain") at the terminus of the laminin A chain (Sephel et al., 1989).

Alveolar Formation Inhibited by SINNNR (SEQ ID NO:4)

Figure 6B:
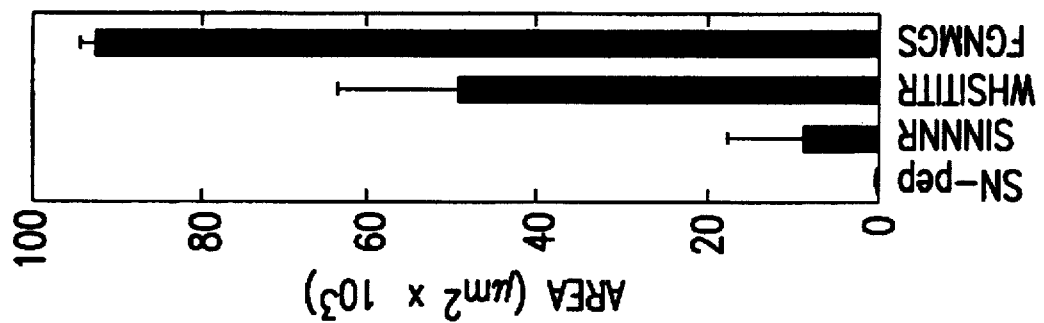
FIGS. 6A–6B. Alveolar formation is inhibited by SN-peptide (SEQ ID NO:7), further defined by trypsin digestion to SINNNR (SEQ ID NO:4). (A) Dose-dependent inhibition of alveolar formation by SN-peptide (SEQ ID NO:7) (○) and its amino-terminal 6-mer SINNNR (SEQ ID NO:4) (□). The carboxy-terminal 6-mer FGNMGS (SEQ ID NO:5) (●) and middle 8-mer WHSIYITR (SEQ ID NO:6) (△) have minimal or partial effect, respectively. Cells were preincubated with peptides in the same manner as laminin fragments and analyzed on day five. (B) Mean±SD at 700 µM on day five; n=9.
Figure 6A:
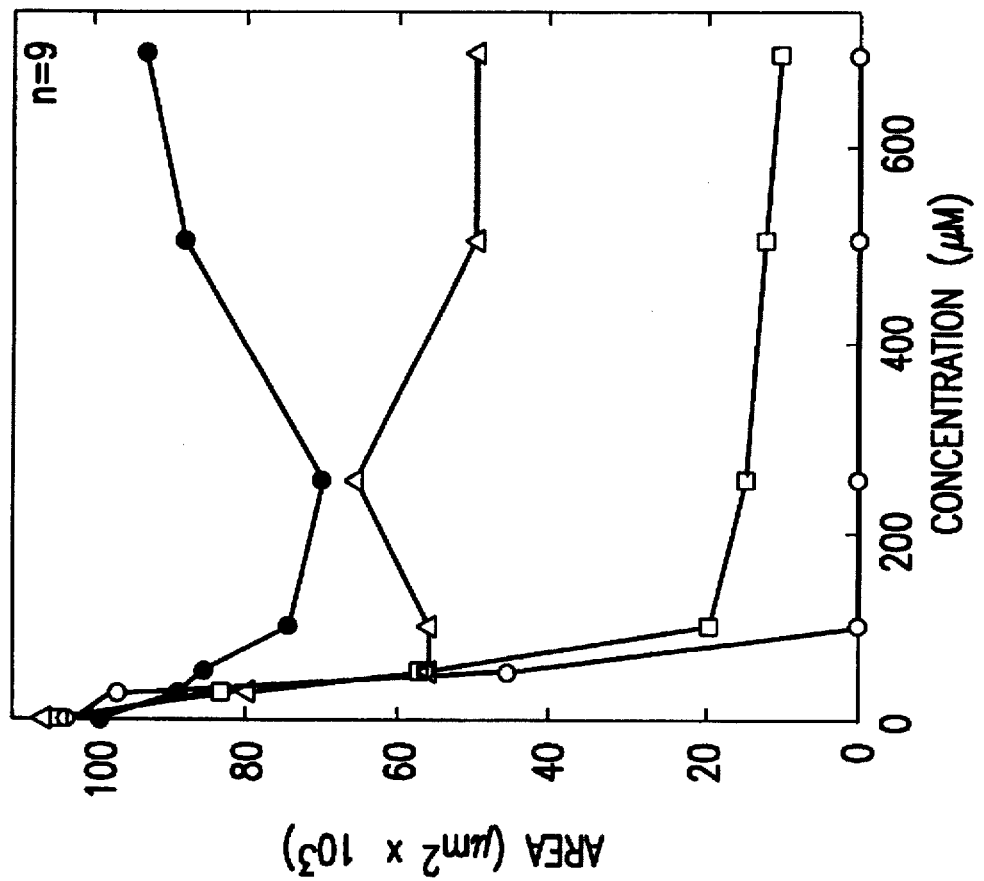

To test this observation directly, the 20-amino acid peptide (SINNNRWHSIYTTRFGNMGS (SEQ ID NO:7); designated "SN-peptide") was synthesized and preincubated at increasing micromolar amounts with freshly isolated dispersed type II alveolar cells prior to plating on BMS. SN-peptide (SEQ ID NO:7) inhibited alveolar formation in a dose dependent fashion (FIG. 6; $IC_{50}$ =50 µM) without affecting cell viability, even at the highest micromolar concentration tested (viability 97±1%). Studies were also performed with equimolar amounts of other laminin A chain synthetic peptides including: AASIKVAVSADR (SEQ ID NO:15) (antigen of ab-A[IK]), AASVVIAKSADR (SEQ ID NO:16) (scrambled IKVAV) (SEQ ID NO:20), KQNCLSS-RASFRGCVRNLRLSR (SEQ ID NO:17) (proposed binding site for α3β1 integrin), and RGDS (functionally equivalent to P1 fragment cell adhesion site RGDN) (SEQ ID NO:18) however, all had no effect on alveolar formation (Table II). To define further the alveolarization site, the SN-peptide was trypsin digested, generating the smaller peptides SINNNR (SEQ ID NO:4), WHSIYTTR (SEQ ID NO:6), and FGNMGS (SEQ ID NO:5). Each was HPLC purified, sequenced, and preincubated with type II alveolar cells at increasing micromolar concentrations. Only SINNNR (SEQ ID NO:4) was inhibitory (FIG. 6; IC50=68 µM).

SN-Peptide and SINNNR have Cell Adhesion Activity

Figure 7A:
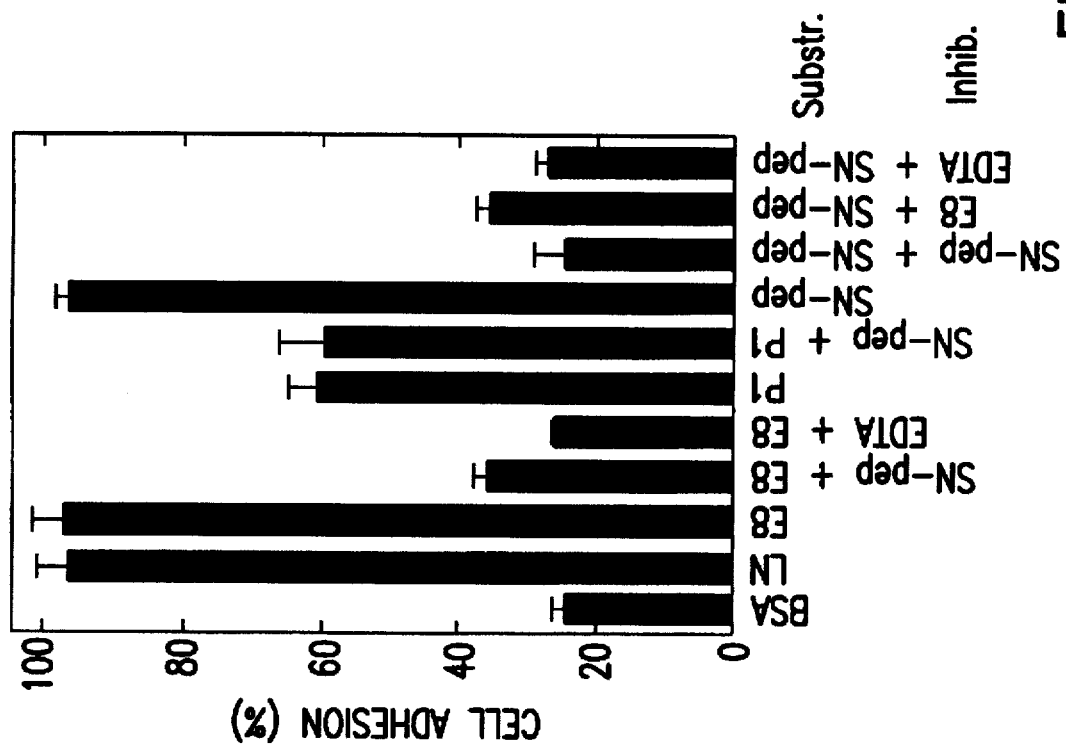
FIGS. 7A–7B. Cells adhere to SN-peptide (SEQ ID NO:7) in an E8 fragment and 2 mM EDTA inhibitable manner. (A) Adhesion of type II alveolar cells to laminin, E8 fragment, and SN-peptide (SEQ ID NO:7) but not BSA. Preincubation of type II cells with E8 fragment competitively inhibited SN-peptide (SEQ ID NO:7) adhesion whereas P1 fragment did not. (B) Adhesion of HT1080 cells to SN-peptide (SEQ ID NO:7) and laminin, with BSA as the negative control. E8 fragment inhibited HT1080 cell adhesion to SN-peptide (SEQ ID NO:7). Similarly, SN-peptide (SEQ ID NO:7) inhibited adhesion to ED8 fragment and SN-peptide (SEQ ID NO:7) but not to P1 fragment. Preincubation of 2 mM EDTA with HT1080 cells inhibited adhesion to SN-peptide (SEQ ID NO:7). Coating and inhibitor concentrations were both 100 µM corresponding to the inhibiting amounts used in alveolar formation five day time course experiments. Values in A and B represent the mean±SD; n=9.

How might the SN-peptide site drive alveolar morphogenesis? One possibility is via cell adhesion, a fundamental requirement of kidney epithelial morphogenesis for which E8 fragment is thought to play a key role (Klein et al., 1988). To examine this possibility, cell adhesion assays were carried out using SN-peptide (SEQ ID NO:7) and SINNNR (SEQ ID NO:4) in the presence or absence of soluble inhibitors, or after preincubation with antibody. Both type II alveolar (FIG. 7A) and HT1080 (FIG. 7B) human fibrosarcoma cells adhered to SN-peptide (SEQ ID NO:7) and SINNNR (SEQ ID NO:4) (Table III) at levels similar to E8 fragment or intact laminin, an interaction which was inhibited by preincubation with equimolar amounts of laminin E8 or SN-peptide (SEQ ID NO:7) but not P1 fragment (FIGS. 7A and B).

TABLE III

SN-peptide (SEQ ID NO: 7) and SINNNR (SEQ ID NO: 4) Adhesion Activity

| Substrate | Percent cell attachment |
| --- | --- |
| Laminin | 80 ± 0.02 |
| E8 fragment | 78 ± 0.05 |
| SN-peptide (SEQ ID NO: 7) | 76 ± 0.02 |
| SINNNR (SEQ ID NO: 4) | 65 ± 0.09 |
| BSA | 21 ± 0.03 |

Adhesion of HT1080 cells to SN-peptide, SINNNR, laminin, and E8 fragment with BSA as the negative control; coated at 35 µM. Data represents mean ± SD from three experiments performed in triplicate.

Figure 7B:
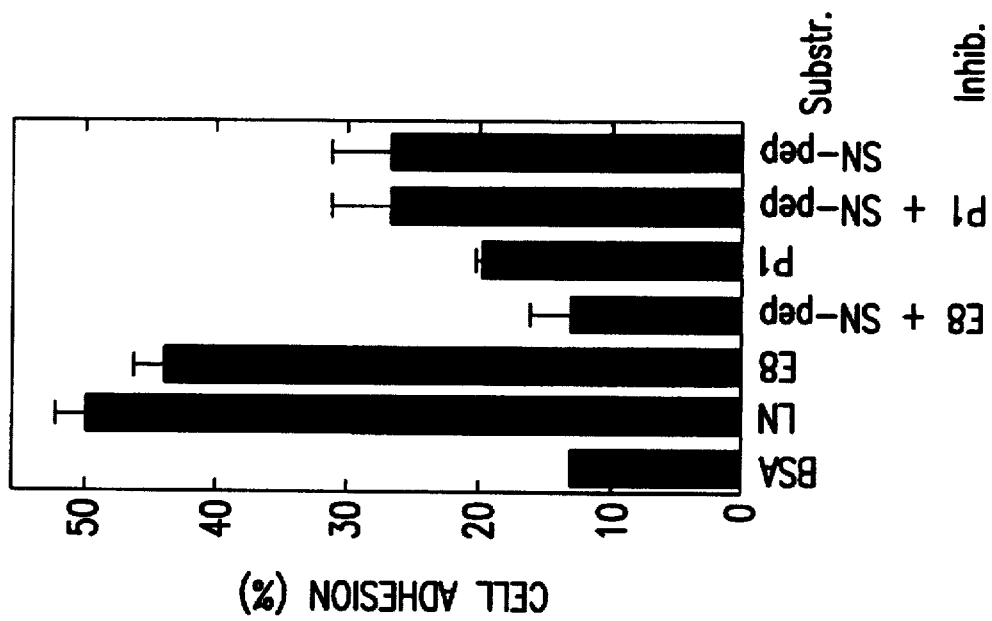

Similarly, ab-A[SN] but not ab-a[IK] inhibited adhesion to SN-peptide (SEQ ID NO:7), SINNNR (SEQ ID NO:4), and E8 without affecting adhesion to P1 (not shown). In reciprocal experiments, adhesion to E8 was completely inhibited by an equimolar amount of SN-peptide (FIG. 7B). In addition, preincubation with 2 mM EDTA was inhibitory (FIG. 7B) suggesting that SN-peptide adhesion was perhaps mediated via an integrin receptor which requires divalent cations for function (Hynes, 1992).

To determine whether SN-peptide (SEQ ID NO:7) and SINNNR (SEQ ID NO:4) were conserved among different species (Table IV), the FastA and BestFit programs revealed that SN-peptide (SEQ ID NO:7) has 65% identity and 85% similarity over the same 20-amino acid residues in human (Haaparanta et al., 1991; Nissinen et al., 1991) laminin A chain. SINNNR (SEQ ID NO:4) displayed 50% identity and 83% similarity. Compared with merosin and Drosophila laminin A chain (Garrison et al., 1991; Hortsch and Goodman, 1991), SN-peptide (SEQ ID NO:7) was 30% and 21% identical and 47% and 40% similar, respectively (Table IV).

Since the laminin A chain is replaced by the A chain homologue, merosin, in some organs (Ehrig et al., 1990; Engvall et al., 1990; Sanes et al., 1990), the presence of laminin A chain in rat lung alveolar basement membranes was investigated. Fetal lung was probed with antibody ab-a[IK] (FIG. 8) and ab-A[SN], through Western blotting (FIG. 8A) and immunofluorescence (FIG. 8C), revealing that laminin A chain was readily detectable in late gestation rat alveolar basement membranes, as had been observed earlier for mouse lung (Klein et al., 1990; Schuger et al., 1991).

Example 2

Materials and Methods

Cell Lines

HT 1080 human fibrosarcoma were obtained from the American Type Culture Collection (Rockville, Md.), F9 mouse teratocarcinoma were kindly supplied by Dr. C. Damsky (UCSF, San Francisco, Calif.). Media used included MEM‡ containing 10% FBS (HT1080 cells); DMEM supplemented with 10% FBS and 2 mM glutamine (F9 cells). All media and sera were from Gibco BRL (Gaithersburg, Md.).

Substrates

Mouse laminin-1 was prepared according to the Kleinman et al (Kleinman 1982) method, or purchased from Upstate Biotechnology Inc. (Lake Placid N.Y.). Collagen I was purchased from Collaborative Biomedical Products (Bedford Mass.). Fragment E8, isolated from mouse laminin-1, was generously supplied by Dr. Peter Yurchenco (Robert Wood Johnson Medical School, Piscataway, N.J.). Sn-peptide (SINNNRWHSIYITRFGNMGS (SEQ ID NO:7) ; amino acids 2179–2198 from mouse laminin α1† chain; Matter 1994) was synthesized by the Bimolecular Research Facility (University of Virginia). Also synthesized was SN-peptide with a COOH-terminal cysteine for column coupling. The subsequence SINNNR (SEQ ID NO:4), which is somewhat less active than SN-peptide, was not used in these initial studies. All synthetic peptides were purified by reverse phase HPLC, and verified by NH$_2$-terminal sequencing and mass spectrometry.

Antibodies

Inhibitory mouse anti-human mabs specific for the α$_2$ (P1E6), α$_3$ (P1B5), α$_4$ (P4C2), α$_5$ (P1D6) and β$^1$ (P4C10; ref 25–27) integrin subunits were purchased from Gibco BRL (Gaithersburg, Md.). Inhibitory rat anti-mouse α$_6$ integrin subunit mab GoH3 (Sonnenberg 1990) was kindly provided by Dr. A. Sonnenberg (The Netherlands Cancer Institute, Amsterdam, The Netherlands) and also purchased from Amac inc. (Westbrook, Me.). The partially blocking mouse anti-human β$_4$ integrin subunit mab UM-A9 was kindly provided by Dr. T. Carey (University of Michigan, Ann Arbor MI; Van Wacs 1991). Also used was the partially blocking mouse anti-human β$_4$ integrin subunit mab 3E1 (Hessle 1984) purchased from Gibco BRL (Gaithersburg, Md.).

Cell Adhesion Assay

Cell adhesion studies were carried out using the Aumailley and Timpl (Aumailley 1986) method. 96-well culture plates (Costar, Cambridge, Mass.) coated overnight (4° C.) in triplicate with increasing micromolar amounts of SN-peptide (SEQ ID NO:7), fragment E8, laminin-1 or BSA (diluted in water) were blocked with 1% BSA (Sigma Chemical Co., St. Louis Mo.) for 4 hrs and incubated with cells (3×10$^5$ cell/ml) in serum-free medium for 60 min (37° C.). Wells were washed twice with medium, fixed with glutaraldehyde, stained with crystal violet, treated with Triton X-100 and analyzed in a ELISA plate reader (Molecular Devives, Menlo Park, Calif.) at 595 nm. For inhibition experiments, plates were coated in triplicate with subsaturating micromolar concentrations of fragment E8 (0.05 μM) or SN-peptide (SEQ ID NO:7) (2.5 μM for HT1080, 5 μM for F9) individually determined from dose response studies to support adhesion at a level 50% of maximum per substrate. Prior to plating, an equal volume of cells (6×10$^5$ cells/ml) and media-diluted antibodies were co-incubated for 45 min at room temperature with gentle agitation every 10 min. Plates were processed as described above, with data expressed as mean±SEM. To test the effect of inhibitory anti-integrin antibodies on cell viability, the MTT assay (Chemicon International, Inc. Temecula Calif.) was used. Coating efficiency was determined by supplementation of substrate with a minor amount of $^{125}$I-labeled fragment E8 of SN-peptide according to the method of Aumailley et al (Aumailley 1987). Coated wells were washed with DMEM and treated with 2M NaOH to release radioactivity for analysis in a gamma counter. Absorption was 0.2% and 1.7% at half-maximal coating levels of SN-peptide and E8, respectively.

Preparation of Affinity Columns

SN-peptide (SEQ ID NO:7) was coupled at 1 mg/ml gel to SulfoLink (Pierce, Rockford Ill.) through an added COOH terminal cysteine according to manufacturer's suggestions. As a control, BSA as reduced with 2-mercaptoethylamine, separated on a Sephadex G-25 column and coupled with SulfoLink at 4.5 mg/ml gel. Coupling efficiencies were 90–95%.

Cell Surface Labeling and Affinity Chromatography

Cells were biotinylated according to the Stephens et al (Stephens 1993) method using 50 μg/ml NHS-LC biotin (pierce, Rockford Ill.). Lysates were centrifuged. Supernatants passed over a blank SulfoLink precolumn and then incubated for 6 hrs. at 4° C. with paired columns of immobilized SN-peptide and BSA. Unbound material was removed by washing with 20 column volumes of running buffer (50 mM Tris, 50 mM octyl-β-D-glucopyranoside, 100 mM NaCl, 5 mM MnCl$_2$, 2 mM PMSF, pH 7.4), followed by elution of bound receptor. SN-peptide columns were eluted with running buffer containing 10 mM EDTA in place of MnCl$_2$. Control columns were run in parallel using the same reagents. Equal aliquots of column fractions were acetone precipitated, separated by 8% SDS PAGE, transferred to nitrocellulose and detected with streptavidin-peroxidase (Amersham, Arlington Heights, Ill.) using the ECL chemiluminescence method.

Immunoprecipitation

Column fractions were precleared for 30 min with protein G agarose (Pierce, Rockford, Ill.), incubated with GoH3 anti-α$_6$ (1 μg/ml) or rat IgG (1 μg/ml) overnight and precipitated with protein G agarose using a goat anti-rat bridge, all at 4° C. Washing was performed as described by Stephens et al (Stephens 1993). Following boiling, samples were separated by 8% SDS PAGE in the absence of DTT, transferred to nitrocellulose and detected as above.

Results

Dose Dependent Cell Adhesion to SN-peptide

Figure 9:
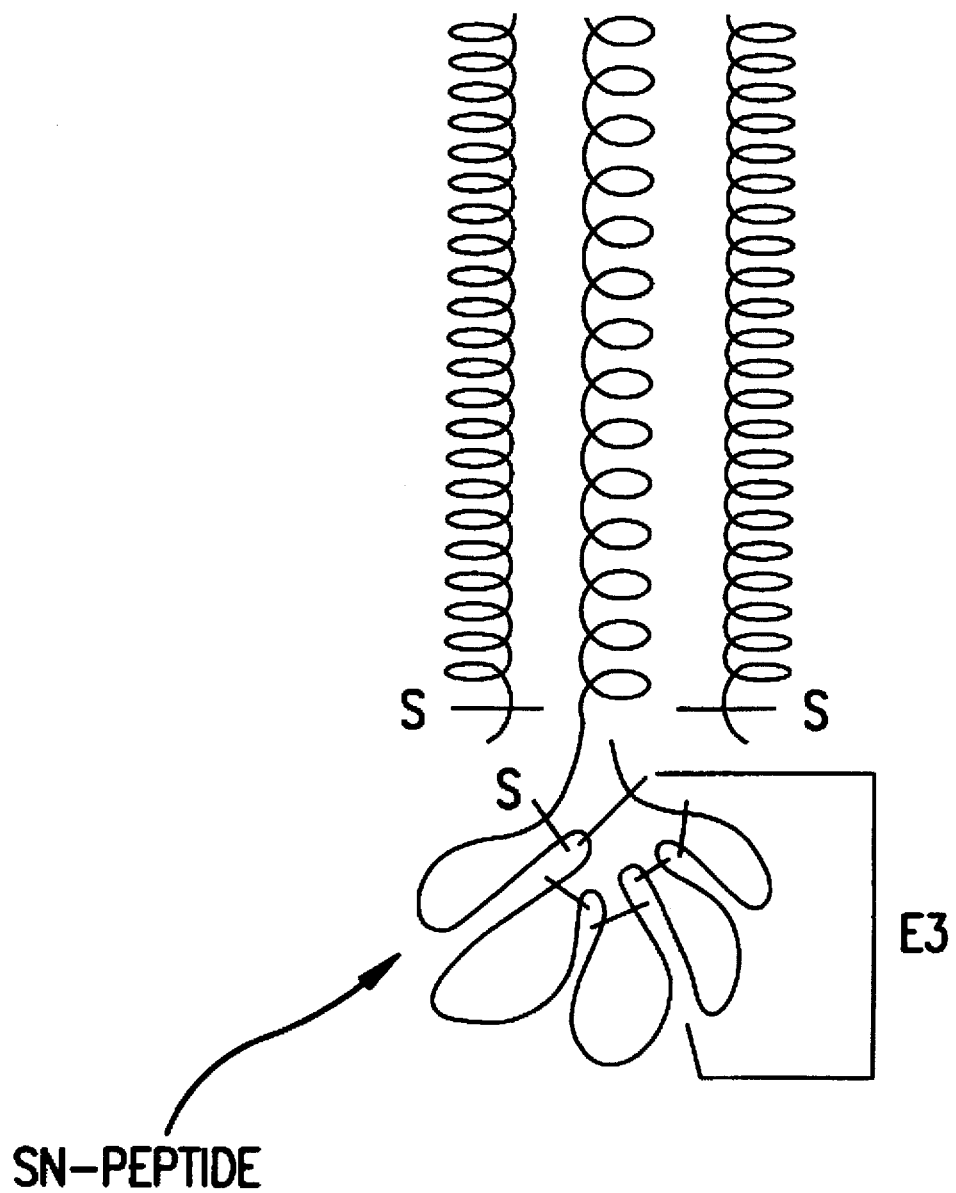
FIG. 9. Schematic diagram of the laminin-1 E8 region illustrating the location of SN-peptide site in the first loop of the globular ('G') domain. The laminin α1 chain forms the G domain and contributes to the rod consisting of β1 and γ1 chains. SN-peptide (SEQ ID NO:7) (arrow) corresponds to amino acids 2179–2198. The last two loops form the E3 domain.

SN-peptide (SEQ ID NO:7) was originally identified by its ability to inhibit lung alveolar formation in vitro and subsequently to support fragment E8 dependent adhesion of rat type II alveolar and human HT1080 cells (Matter 1994). SN-peptide (SEQ ID NO:7) corresponds to a site (FIG. 9) within the first loop of the laminin-1 G domain (amino acids 2179–2198 from α1 chain). Since HT1080 cell adhesion of SN-peptide (SEQ ID NO:7) was cation dependent (Matter 1994), the possibility that the receptor(s) was an integrin(s) was pursued.

Figure 10A:
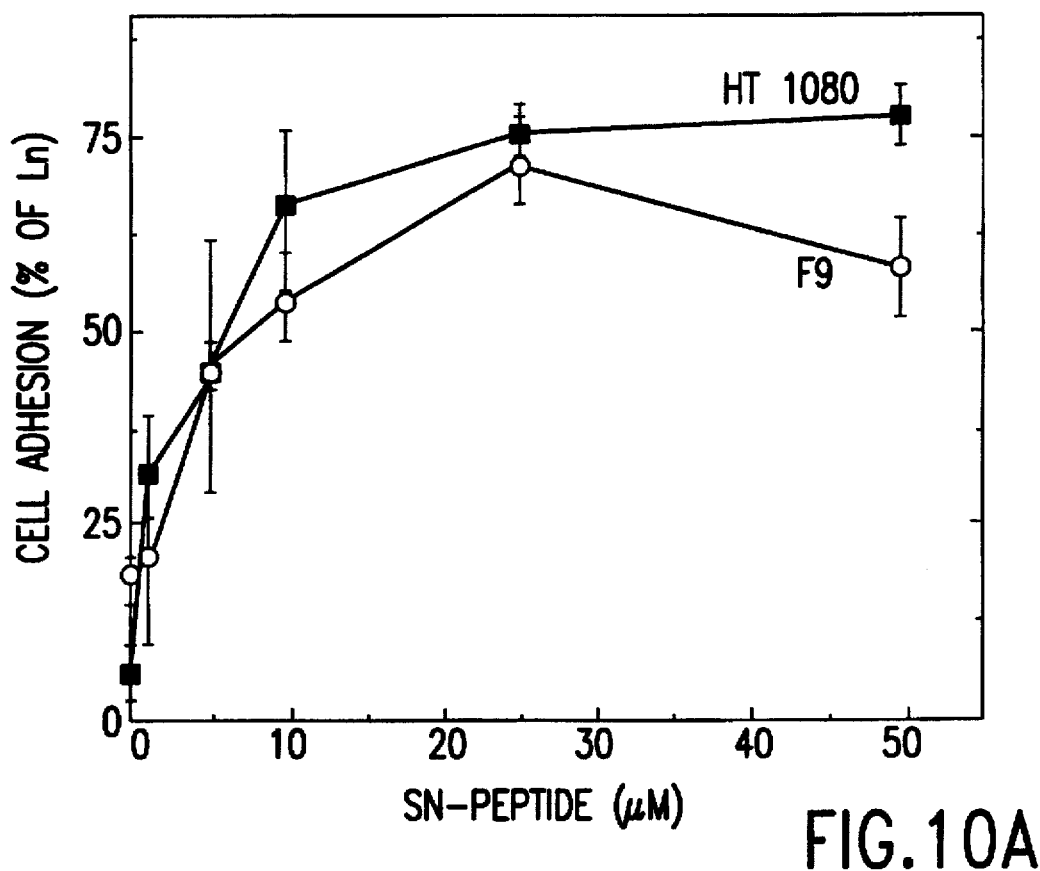
FIGS. 10A–10B. Dose-dependent adhesion of HT1080 and F9 cells to SN-peptide (SEQ ID NO:7). Adhesion of both cell lines is maximal using a 25 µM coating solution (HT1080, closed square; F9, open circle). Inset, comparative adhesion of fragment E8 in which maximal adhesion is observed using a 0.5 µM coating solution. Data from three or more experiments each carried out in triplicate expressed as percent of adhesion to a maximal level of coated laminin (coating solution 0.1 µM). BSA negative control values have been subtracted, and were 10% or less of the maximum experimental value.
Figure 10B:
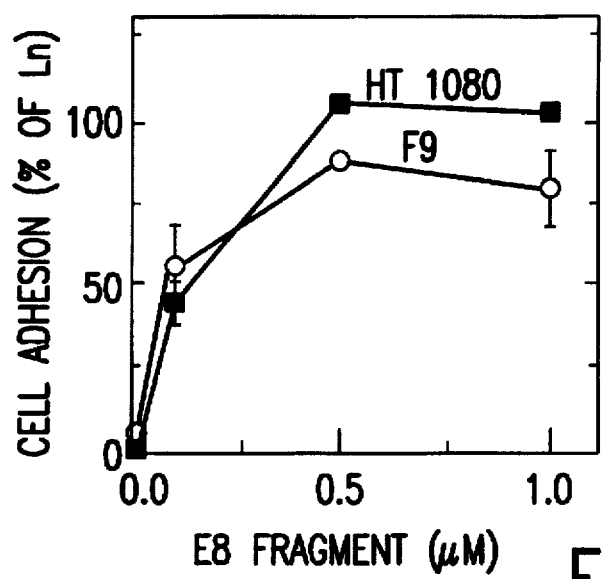

Initial experiments investigated the SN-peptide coating concentration required for half-maximal cell adhesion (FIG. 10), the coating level used in subsequent antibody inhibition studies. Both HT1080 and mouse F9 cells bound to SN-peptide in a dose-dependent manner with half-maximal adhesion using a coating solution of 2.5–5 µM. Plateau adhesion was 70% of that obtainable with laminin (FIG. 10) and approximately 10% of the cells spread (not shown). Corresponding values for fragment E8 were 0.05 µM and 80 to 100% (FIG. 10, inset) with complete spreading (not shown). To determine whether these differences were in part due to differential substrate absorption, trace amounts of iodinated SN-peptide (SEQ ID NO:7) or E8 were included, revealing absorption to be 8.5 fold less for SN-peptide (SEQ ID NO:7). Correcting half-maximal coating values for substrate actually absorbed point to a 6 fold difference in adhesion activity between SN-peptide and E8.

Figure 11A:
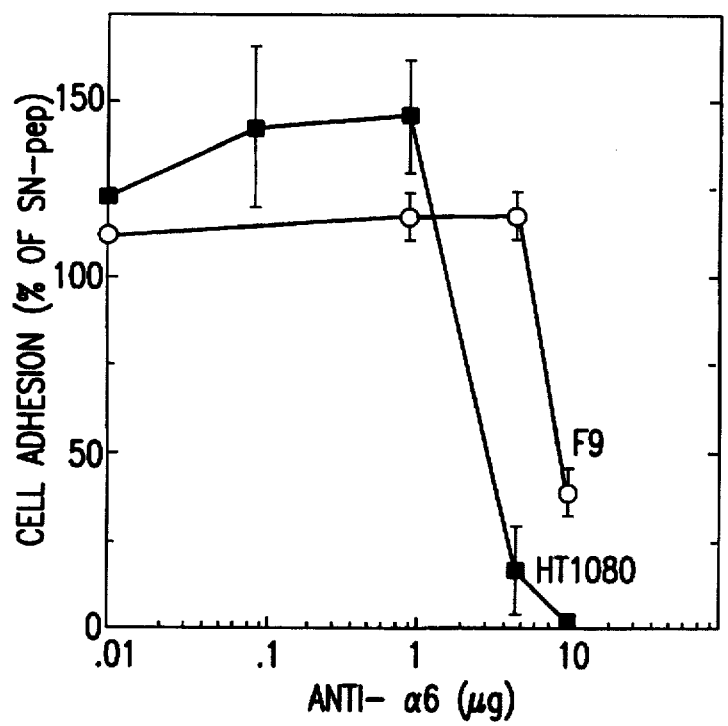
FIGS. 11A–11C. SN-peptide dependent cell adhesion is inhibited by anti-α6, anti-β1 and -β4 integrin mabs. a. Dose-dependent inhibition of HT1080 and F9 cell adhesion by the anti-α6 integrin subunit mab GoH3 (HT1080, closed square; F9, open circle). b. β1 specific mab P4C10 (50 µg/well) inhibits HT1080 (closed bars) and F9 (open bars) cell adhesion. Anti-β4 mab 3E1 inhibits F9 but not HT1080 adhesion. Combination of anti-β1 and anti-β4 was not additive. c. No inhibition of SN peptide-dependent cell adhesion is observed with anti-α2 - anti-α5 subunit specific antibodies (10 µg/well; HT1080). Values represent four experiments each carried out in triplicate. BSA negative control values have been subtracted.

Antibodies to $\alpha_6$, $\beta_1$ and $\beta_4$ Integrin Subunits Inhibit Adhesion to SN-Peptide Human HT1080 cells express a number of integrin subunits including: $\alpha_2$, $\alpha_3$, $\alpha_5$, $\alpha_6$, and $\beta_1$ (von der Mark 1991). Mouse F9 cell subunits include: $\alpha_3$, $\alpha_5$, $\alpha_6$, $\beta_1$, $\beta_3$, $\beta_5$ and a small amount of $\beta_4$ (Stephens 1993). Unlike human integrins, few neutralizing anti-mouse subunit mabs exist. Advantage was therefore taken of HT1080 cells whose capacity to adhere to SN-peptide (SEQ ID NO:7) was found to be complete blocked by the anti-$\alpha_6$ subunit mab GoH3 (FIG. 11a). In contrast, neutralizing anti-$\alpha_2$, -$\alpha_3$, -$\alpha_4$ and -$\alpha_5$ mabs had no effect (FIG. 3a, inset). Also inhibitory was the $\beta_1$ specific mab P4C10, but not the $\beta_4$ specific mabs 3E1 (FIG. 11b) and UM-A9 (not shown). Cell viability in the presence of inhibitory antibodies was 74–100%.

Figure 11B:
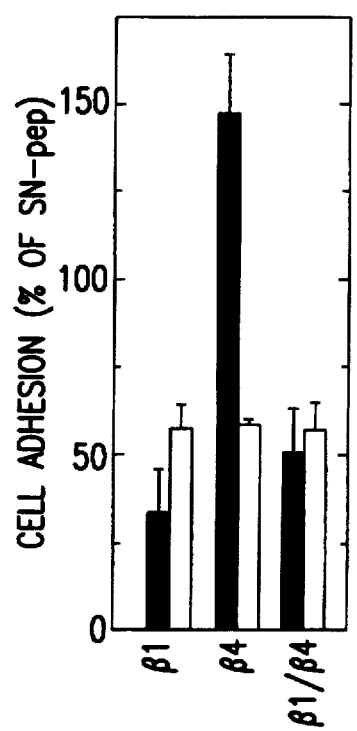
Figure 11C:
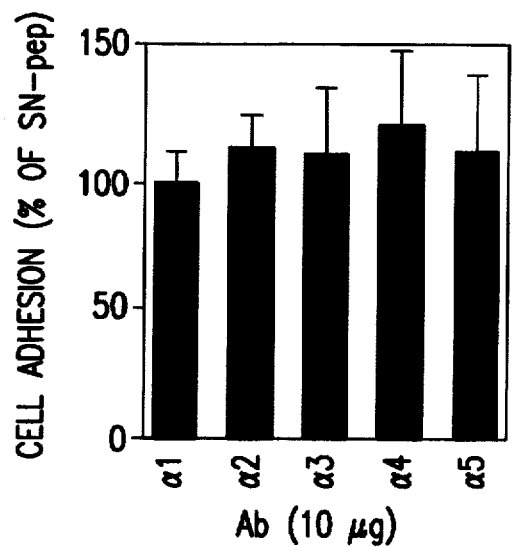

Examination of F9 cells confirmed the ability of the $\alpha_6$ and $\beta_1$ specific mabs to inhibit adhesion to SN-peptide (FIG. 11). Differing from HT1080 was a sensitivity to anti-$\beta_4$ mab (FIG. 11b), which was not additive when both anti-$\beta_1$ and anti-$\beta_4$ mabs were combined (FIG. 11b).

$\alpha_6 \beta_1$ Binds to SN-Peptide Affinity Columns

Affinity chromatography was used to evaluate $\alpha_6 \beta_1$ binding to SN-peptide (SEQ ID NO:7) (FIG. 12). Sn-peptide columns were incubated with biotinylated F9 cell surface extracts in the presence of $Mn^{+2}$ and washed extensively. Subsequent replacement of $Mn^{+2}$ for EDTA eluted two prominent bands at 135–140 and 120 kDa (FIG. 12). A parallel BSA column was blank (FIG. 12). Immunoprecipitation of the eluate with GoH3 mab yielded the same two prominent bands. The prominent bands therefore correspond to the $\alpha_6$ (upper) and $\beta_1$ (lower) subunit.

---

SEQUENCE LISTING ( 1 ) GENERAL INFORMATION:

( i i i ) NUMBER OF SEQUENCES: 43

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Arg Gly Asp Ser
    1

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Ala Ala Ser Ile Lys Val Ala Val Ser Ala Asp Arg
    1             5                        10

( 2 ) INFORMATION FOR SEQ ID NO:3:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Lys Gln Asn Cys Leu Ser Ser Arg Ala Ser Phe Arg Gly Cys Val Arg
 1               5                  10                  15
Asn Leu Arg Leu Ser Arg
             20
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Ser Ile Asn Asn Asn Arg
 1               5
```

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Phe Gly Asn Met Gly Ser
 1               5
```

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Trp His Ser Ile Tyr Ile Thr Arg
 1               5
```

( 2 ) INFORMATION FOR SEQ ID NO:7:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

-continued

```
Ser Ile Asn Asn Asn Arg Trp His Ser Ile Tyr Ile Thr Arg Phe Gly
1               5                   10                  15
Asn Met Gly Ser
            20
```

(2) INFORMATION FOR SEQ ID NO:8:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Ser Ile Asn Asn Asn
1               5
```

(2) INFORMATION FOR SEQ ID NO:9:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Ile Asn Asn Asn Arg
1               5
```

(2) INFORMATION FOR SEQ ID NO:10:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Pro Ile Asp Asp Asn Arg Trp His Ser Ile His Val Ala Arg Phe Gly
1               5                   10                  15
Asn Ile Gly Ser
            20
```

(2) INFORMATION FOR SEQ ID NO:11:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Pro Ile Asp Asp Asn
1               5
```

(2) INFORMATION FOR SEQ ID NO:12:

(i) SEQUENCE CHARACTERISTICS:
        (A) LENGTH: 5 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO:12:

Ile Asp Asp Asn Arg
    1               5

(2) INFORMATION FOR SEQ ID NO:13:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Pro Ile Asp Asp Asn Arg
    1               5

(2) INFORMATION FOR SEQ ID NO:14:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Tyr Ile Gly Ser Arg
    1               5

(2) INFORMATION FOR SEQ ID NO:15:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Ala Ala Ser Ile Lys Val Ala Val Ser Ala Asp Arg
    1               5                   10

(2) INFORMATION FOR SEQ ID NO:16:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Ala Ala Ser Val Val Ile Ala Lys Ser Ala Asp Arg
    1               5                   10

(2) INFORMATION FOR SEQ ID NO:17:

(i) SEQUENCE CHARACTERISTICS:
        (A) LENGTH: 22 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO:17:

Lys Gln Asn Cys Leu Ser Ser Arg Ala Ser Phe Arg Gly Cys Val Arg
1               5                   10                  15

Asn Leu Arg Leu Ser Arg
            20

(2) INFORMATION FOR SEQ ID NO:18:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:18:

Arg Gly Asp Asn
1

(2) INFORMATION FOR SEQ ID NO:19:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:19:

Pro Ile Asp Asp Asn Arg Trp His
1               5

(2) INFORMATION FOR SEQ ID NO:20:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:20:

Ile Lys Val Ala Val
1               5

(2) INFORMATION FOR SEQ ID NO:21:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:21:

Arg Asn Ile Ala Glu Ile Ile Lys Asp Ile
1               5                   10

(2) INFORMATION FOR SEQ ID NO:22:

(i) SEQUENCE CHARACTERISTICS:

(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:22:

Pro Ile Asp Asp Asn Arg Trp
1               5

(2) INFORMATION FOR SEQ ID NO:23:

(i) SEQUENCE CHARACTERISTICS:
(A) LENGTH: 17 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:23:

Ser Ile Asn Asn Asn Arg Trp His Ser Ile Tyr Ile Thr Arg Phe Gly
1               5                   10                  15
Asn (2) INFORMATION FOR SEQ ID NO:24:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:24:

Ser Ile Asn Asn Asn Arg Trp His Ser Ile Tyr Ile Thr Arg Phe Gly
1               5                   10                  15

(2) INFORMATION FOR SEQ ID NO:25:

(i) SEQUENCE CHARACTERISTICS:
(A) LENGTH: 15 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:25:

Ser Ile Asn Asn Asn Arg Trp His Ser Ile Tyr Ile Thr Arg Phe
1               5                   10                  15

(2) INFORMATION FOR SEQ ID NO:26:

(i) SEQUENCE CHARACTERISTICS:
(A) LENGTH: 14 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:26:

Ser Ile Asn Asn Asn Arg Trp His Ser Ile Tyr Ile Thr Arg
1               5                   10

(2) INFORMATION FOR SEQ ID NO:27:

( i ) SEQUENCE CHARACTERISTICS:
 ( A ) LENGTH: 13 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:27:

Ser Ile Asn Asn Asn Arg Trp His Ser Ile Tyr Ile Thr
1               5                       10

( 2 ) INFORMATION FOR SEQ ID NO:28:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:28:

Ser Ile Asn Asn Asn Arg Trp His Ser Ile Tyr Ile
1               5                       10

( 2 ) INFORMATION FOR SEQ ID NO:29:

( i ) SEQUENCE CHARACTERISTICS:
  ( A ) LENGTH: 11 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:29:

Ser Ile Asn Asn Asn Arg Trp His Ser Ile Tyr
1               5                       10

( 2 ) INFORMATION FOR SEQ ID NO:30:

( i ) SEQUENCE CHARACTERISTICS:
  ( A ) LENGTH: 10 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:30:

Ser Ile Asn Asn Asn Arg Trp His Ser Ile
1               5                       10

( 2 ) INFORMATION FOR SEQ ID NO:31:

( i ) SEQUENCE CHARACTERISTICS:
  ( A ) LENGTH: 9 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:31:

Ser Ile Asn Asn Asn Arg Trp His Ser
1               5

( 2 ) INFORMATION FOR SEQ ID NO:32:

( i ) SEQUENCE CHARACTERISTICS:
   ( A ) LENGTH: 8 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:32:

Ser Ile Asn Asn Asn Arg Trp His
1               5

( 2 ) INFORMATION FOR SEQ ID NO:33:

( i ) SEQUENCE CHARACTERISTICS:
   ( A ) LENGTH: 7 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:33:

Ser Ile Asn Asn Asn Arg Trp
1               5

( 2 ) INFORMATION FOR SEQ ID NO:34:

( i ) SEQUENCE CHARACTERISTICS:
   ( A ) LENGTH: 19 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:34:

Pro Ile Asp Asp Asn Arg Trp His Ser Ile His Val Ala Arg Phe Gly
1               5                   10                  15

Asn Ile Gly ( 2 ) INFORMATION FOR SEQ ID NO:35:

( i ) SEQUENCE CHARACTERISTICS:
   ( A ) LENGTH: 18 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:35:

Pro Ile Asp Asp Asn Arg Trp His Ser Ile His Val Ala Arg Phe Gly
1               5                   10                  15

Asn Ile ( 2 ) INFORMATION FOR SEQ ID NO:36:

( i ) SEQUENCE CHARACTERISTICS:
   ( A ) LENGTH: 17 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:36:

Pro Ile Asp Asp Asn Arg Trp His Ser Ile His Val Ala Arg Phe Gly

Asn (2) INFORMATION FOR SEQ ID NO:37:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

Pro Ile Asp Asp Asn Arg Trp His Ser Ile His Val Ala Arg Phe Gly
1               5                   10                  15

(2) INFORMATION FOR SEQ ID NO:38:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

Pro Ile Asp Asp Asn Arg Trp His Ser Ile His Val Ala Arg Phe
1               5                   10                  15

(2) INFORMATION FOR SEQ ID NO:39:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

Pro Ile Asp Asp Asn Arg Trp His Ser Ile His Val Ala Arg
1               5                   10

(2) INFORMATION FOR SEQ ID NO:40:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:40:

Pro Ile Asp Asp Asn Arg Trp His Ser Ile His Val Ala
1               5                   10

(2) INFORMATION FOR SEQ ID NO:41:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:41:

```
Pro  Ile  Asp  Asp  Asn  Arg  Trp  His  Ser  Ile  His  Val
1              5                        10
```

( 2 ) INFORMATION FOR SEQ ID NO:42:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:42:

```
Pro  Ile  Asp  Asp  Asn  Arg  Trp  His  Ser  Ile  His
1              5                        10
```

( 2 ) INFORMATION FOR SEQ ID NO:43:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:43:

```
Pro  Ile  Asp  Asp  Asn  Arg  Trp  His  Ser  Ile
1              5                        10
```

REFERENCES CITED

Abrahamson et al, 1989. *J. Cell. Biol.* 109:3477–3491.

Adamson et al, 1989. in vitro Cell. & Dev. Biol. 25:494–502.

Akiyama et al., 1990. *Biochem Biophys. Acta.* 1031, 91–110.

Albelda and Buck, 1990. *FASEB J.* 4: 2868–2879.

Aumailley et al, 1987 *J. Biol. Chem.* 262, 11532–11538.

Aumailley et al, 1990. *Exp. Cell Res.* 188; 55–66.

Aumailley and Timpl, 1986. *J. Cell Biol.* 103:1569–1575.

Ballard, 1986. Hormones and lung maturation. Springer-Verlag, Berlin. p. 354.

Beck et al, 1990. *FASEB (Fed. Am. Soc. Exp. Biol.) J.* 4:148–160.

Blau et al, 1988. *J. Cell. Physiol.* 136:203–214.

Burgeson, 1994. *Matrix Biol.* 14: 209–211.

Burri, 1991. Postnatal development and growth. In The Lung. Vol. I, R. G. Crystal, J. B. West, P. J. Barnes, N. S., E. R. Weibel, editors. Raven Press, New York, 235–246.

Carter et al, 1990 *J. Cell Biol* 100, 1287–1404.

Chammas et al, 1991 *J. Biol. Chem.* 266, 3349–3355.

Chen, W. -T., et al, 1986. *J. Cell Biol.* 103:1073–1090.

Cooper et al, 1991, *J. Cell Biol.* 115: 843–850.

Dayhoff, M. O. et al., 1978. A model of evolutionary change in proteins. In atlas of Protein Sequence and Structure. Vol. 5., M. O. Dayhoff, editor. Nat. Biomed. Res. Foundation, Washington, D.C., 345 Deutzmann. et al, 1990. *Eur. J. Biochem.* 191:513–522.

Diglio and Kikkawa, 1977. *Lab. Invest.* 37:622–631.

Drago et al, 1991. *Exp. Cell Res.* 192:256–265.

Edelson et al, 1989. *Am. Rev. Respit. Dis.* 140:1398–1404.

Ehrig et al, 1990. *Proc. Natl. Acad. Sci., USA* 87:3264–3268.

Entel, Jr., 1992. *Biochemistry,* 31:10643–10651.

Engvall et al, 1990. *Cell Regul.* 1:731–740.

Garrison et al, 1991. *J. Biol. Chem.* 266:22899–22904.

Gehisen et al, 1992. *J. Cell Biol.* 117:449–459.

Gil et al, 1984. *J. Histochem. Cytochem.* 32:230–238.

Haaparanta et al, 1991. *Matrix* 11:151–160.

Hawgood, 1991. Surfactant; composition, structure and metabolism. In The Lung. Vol. I, R. G. Crystal, J. B. West, P. J. Barnes, N. S. Cherniack, and New York. 247–261.

Hay, E. D. (1993) *Curr. Opin. Cell Biol.* 5, 1029–1035.

Hessle et al, 1984 *Different.* 26, 49–54.

Hogervorst et al, 1991 *Eur. J. Biochem.* 199, 425–433.

Hortsch and Goodman, 1991. *Annu. Rev. Cell Biol.* 7:505–557.

Hynes, 1992. *Cell* 69:11–25.

Hynes and Lander, (1992) *Cell* 68: 303–322.

Kibbey et al, *Proc. Natl. Acad. Sci., USA* 90:10150–10153.

Klein et al, 1988. *Cell* 55:331–341.

Klein et al, 1990. *Development.* 110:822–837.

Kleinman et al, 1986. *Biochemistry* 25:312–318.

Kleinman et al, 1982. *Biochem.* 24, 6188–6193.

Kramer et al, 1991. *Cell Regulation* 2: 805–817.

Labarca and Paigen, 1980. *Biochemistry* 25:312–318.

Lee et al, 1992. *J. Cell Biol.* 117: 671–678.

Lin et al, 1993. *Cancer Res.* 53: 2950–2953.

Lwebuga-Mukasa, 1991. *Am. Rev. Respir. Dis.* 144:452–457.

Mason and Williams, 1991. Alveolar type II cells. In The Lung, Vol. I, R. G. Crystal, J. B. West, P. J. Barnes, N. S. Cherniack, and New York. 235–246.

Matter and Laurie 1994 *J. Cell Biol.* 124, 1083–1090.

McCarthy et al, 1983. *J. Cell Biol.* 97:772–777.

McGowan, 1992. *FASEB (Fed. Am. Soc. Exp. Biol.) J.* 6:2895–2904.

Mercurio and Shaw, 1991. *Bioassays* 14: 469–473.

Nagai et al, 1991. *J. Cell Biol* 114:1295–1305.

Niessen et al, 1994. *Exp. Cell Res.* 211: 360–367.

Nissinen et al, 1991. *Biochem. J.* 276:369–379.

Obara et al, 1988. *Cell* 53:649–657.

Paulsson, 1992. *Crit. Rev. Biochem. Mol. Biol.* 27:93–127.

Paulsson et al, 1987. *Eur. J. Biochem.* 166:11–19.

Rannels and Rannels, 1988. Isolation and culture of alveolar type II cells for toxicological studies. In Toxicology of the Lung. D. E. Gardner, J. R. Crapo, and E. J. Massaro, editors. Raven Press, New York, 2119–238.

Rannels et al, 1987. *Am. J. Physiol.* 253:C835–C845.

Sanes et al, 1990. *J. Cell Biol.* 111:1685–1699.

Sannes, 1991. *Exp. Lung Res.* 17:639–659.

Sasaki et al, 1988. *J. Biol. Chem.* 263:16536–16544.

Schuger et al, 1991. *Dev. Biol.* 146:531–541.

Schuger et al, 1992. *Dev. Dyn.* 195:43–54.

Sephel et al, 1989. *Biochem. Biophys. Res. Commun.* 162:821–829.

Shannon et al, 1987. *Biochim. Biophys. Acta.* 931:143–156.

Sonnenberg et al., 1990. *J. Cell Biol.* 110:2145–2155.

Sonnenberg et al, 1988. *Nature (London)* 336: 487–489.

Sorokin et al, 1990. *J. Cell Biol.* 111:1265–1273.

Stephens et al, 1993 *J. Cell Biol.* 123, 1607–1620.

Streuli et al, 1991. *J. Cell Biol.* 115:1383–1395.

Sung et al, 1993 *J. Cell Biol.* 123, 1255–1268.

Tashiro et al., 1989. *J. Biol. Chem.* 264:16174–16182.

Terpe et al, 1994. *Histochemistry* 101: 41–49.

Thurlbleck, 1975. *Am. Rev. Respir. Dis.* 111:803–843.

Timpl, 1989. *Eur. J. Biochem.* 180:487–502.

Van Wacs et al, 1991 *Cancer Res.* 51, 2395–2402.

von der Mark et al, 1992. *Kidney International* 41,632–640.

von der Mark et al, 1991. *J. Biol. Chem.* 266: 23593–23601.

Wayner et al, 1988 *J. Cell Biol.* 107, 1881–1891.

Wayner et al, 1989 *J. Cell Biol.* 109, 1321–1330.

Yamada, 1991. *J. Biol. Chem.* 266:12809–12812.

Yurchenco et al., 1993. *J. Biol. Chem.* 268:8356–8365.

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A peptide of the sequence SINNNRWHSIYITRF-GNMG (SEQ ID NO:7) or a peptide fragment thereof containing the subsequence SINNN (SEQ ID NO:8) or INNNR (SEQ ID NO:9).

2. The peptide of claim 1, wherein said peptide contains the subsequence SINNNR (SEQ ID NO:4).

3. The peptide of claim 1, selected from the group consisting of:

SINNNRWHSIYITRFGNMG (SEQ ID NO:7),
SINNNRWHSIYITRFGN (SEQ ID NO:23),
SINNNRWHSIYITRFG (SEQ ID NO:24),
SINNNRWHSIYITRF (SEQ ID NO:25),
SINNNRWHSIYITR (SEQ ID NO:26),
SINNNRWHSIYIT (SEQ ID NO:27),
SINNNRWHSIYI (SEQ ID NO:28),
SINNNRWHSIY (SEQ ID NO:29),
SINNNRWHSI (SEQ ID NO:30),
SINNNRWHS (SEQ ID NO:31),
SINNNRWH (SEQ ID NO:32),
SINNNRW (SEQ ID NO:33),
SINNNR (SEQ ID NO:4),
INNNR (SEQ ID NO:9) and
SINNN (SEQ ID NO:8).

4. A peptide of the sequence PIDDNRWHSIHVARF-GNIGS (SEQ ID NO:10) or a peptide fragment thereof containing the subsequence IDDNR (SEQ ID NO:12) or PIDDN (SEQ ID NO:11).

5. The peptide of claim 4, wherein said subsequence is PIDDNR (SEQ ID NO:13).

6. The peptide of claim 4, wherein said peptide is selected from the group consisting of:

PIDDNRWHSIHVARFGNIGS (SEQ ID NO:10),
PIDDNRWHSIHVARFGNIG (SEQ ID NO:34),
PIDDNRWHSIHVARFGNI ( SEQ ID NO:35),
PIDDNRWHSIHVARFGN (SEQ ID NO:36),
PIDDNRWHSIHVARFG (SEQ ID NO:37),
PIDDNRWHSIHVARF (SEQ ID NO:38),
PIDDNRWHSIHVAR (SEQ ID NO:39),
PIDDNRWHSIHVA (SEQ ID NO:40),
PIDDNRWHSIHV (SEQ ID NO:41),
PIDDNRWHSIH (SEQ ID NO:42),
PIDDNRWHSI (SEQ ID NO:43),
PIDDNRWH (SEQ ID NO:44),
PIDDNRW (SEQ ID NO:22),
PIDDNR (SEQ ID NO:13),
PIDDN (SEQ ID NO:11) and
IDDNR (SEQ ID NO:12).

7. A composition comprising a pharmaceutically acceptable carrier and a peptide of the sequence SINNNRWHSIY-ITRFGNMGS (SEQ ID NO:7) or a peptide fragment thereof containing the subsequence SINNN (SEQ ID NO:8) or INNNR (SEQ ID NO:9).

8. A composition comprising a pharmaceutically acceptable carrier and a peptide of the sequence PIDDNRWHSI-HVARFGNIGS (SEQ ID NO:10) or a peptide fragment thereof containing the subsequence PIDDN (SEQ ID NO:11) or IDDNR (SEQ ID NO:12).

9. A culture dish with a peptide of the sequence SINNNR-WHSIYITRFGNMGS (SEQ ID NO:7) or a peptide fragment thereof containing the subsequence SINNN (SEQ ID NO:8) or INNNR (SEQ ID NO:9).

10. A culture dish with a peptide of the sequence PIDD-NRWHSIHVARFGNIGS (SEQ ID NO:10) or a peptide fragment thereof containing the subsequence PIDDN (SEQ ID NO:11) or IDDNR (SEQ ID NO:12).

11. A method of promoting wound healing, comprising applying to the surface of said wound a peptide of the sequence SINNNRWHSIYITRFGNMGS (SEQ ID NO:7) or a peptide fragment thereof containing the subsequence SINNN (SEQ ID NO:8) or INNNR (SEQ ID NO:9).

12. A method of promoting wound healing, comprising applying to the surface of said wound a peptide of the sequence PIDDNRWHSIHVARFGNIGS (SEQ ID NO:10) or a peptide fragment thereof containing the subsequence PIDDN (SEQ ID NO:11) or IDDNR (SEQ ID NO:12).

13. A method of promoting alveolarization, comprising treating stem cells or progenitor cells isolated from lung tissue with a peptide of the sequence SINNNRWHSIYITRFGNMGS (SEQ ID NO:7) or a peptide fragment thereof containing the subsequence SINNN (SEQ ID NO:8) or INNNR (SEQ ID NO:9).

14. A method of promoting alveolarization, comprising treating stem cells or progenitor cells isolated from lung tissue with a peptide of the sequence PIDDNRWHSIHVARFGNIGS (SEQ ID NO:10) or a peptide fragment thereof containing the subsequence PIDDN (SEQ ID NO:11) or IDDNR (SEQ ID NO:12).

15. A solid support onto which is absorbed a peptide of the sequence PIDDNRWHSIHVARFGNIGS (SEQ ID NO:10) or a peptide fragment thereof containing the subsequence PIDDN (SEQ ID NO:11) or IDDNR (SEQ ID NO:12) absorbed onto a solid support.

16. The solid support of claim 15 which is a cell culture plate, a vascular graft or a prosthetic device.

17. A solid support onto which is absorbed a peptide of the sequence SINNNRWHSIYITRFGNMGS (SEQ ID NO:7) or a peptide fragment thereof containing the subsequence SINNN (SEQ ID NO:8) or INNNR (SEQ ID NO:9).

18. The solid support of claim 17 which is a cell culture plate, a vascular graft or a prosthetic device.

* * * * *